(12) United States Patent
Wangh et al.

(10) Patent No.: US 7,517,977 B2
(45) Date of Patent: Apr. 14, 2009

(54) REAGENTS AND METHODS FOR IMPROVING REPRODUCIBILITY AND REDUCING MISPRIMING IN PCR AMPLIFICATION

(75) Inventors: Lawrence J. Wangh, Auburndale, MA (US); John Rice, Quincy, MA (US); J. Aquiles Sanchez, Framingham, MA (US); Kenneth Pierce, Natick, MA (US); Jesse Salk, Seattle, WA (US); Arthur Reis, Arlington, MA (US); Cristina Hartshorn, Needham, MA (US)

(73) Assignee: Brandeis University, Waltham, MA (US)

( * ) Notice: Subject to any disclaimer, the term of this patent is extended or adjusted under 35 U.S.C. 154(b) by 122 days.

(21) Appl. No.: 11/252,506

(22) Filed: Oct. 17, 2005

(65) Prior Publication Data

US 2006/0177842 A1 Aug. 10, 2006

(51) Int. Cl.
*C07H 21/04* (2006.01)
*C12Q 1/68* (2006.01)
*C12P 19/34* (2006.01)

(52) U.S. Cl. .................. 536/24.3; 435/6; 435/91.1; 435/91.2

(58) Field of Classification Search ................ None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,066,584 A | 11/1991 | Gyllensten et al. | |
| 5,338,671 A | 8/1994 | Scalice et al. | |
| 5,487,972 A | 1/1996 | Gelfand et al. | |
| 5,677,152 A | 10/1997 | Birch et al. | |
| 5,773,258 A | 6/1998 | Birch et al. | |
| 5,925,517 A | 7/1999 | Tyagi et al. | |
| 5,994,056 A | 11/1999 | Higuchi | |
| 6,020,130 A | 2/2000 | Gold et al. | |
| 6,090,552 A * | 7/2000 | Nazarenko et al. | 435/6 |
| 6,150,097 A | 11/2000 | Tyagi et al. | |

FOREIGN PATENT DOCUMENTS

WO WO 02/057479 A2 * 7/2002

WO WO 03/054233 7/2003

OTHER PUBLICATIONS

Nelson et al., "Incorporation of a Non-Nucleotide Bridge into Hairpin Oligonucleotides Capable of High-Affinity Binding t othe Rev Protein of HIV-1," Biochemistry, 1996, vol. 35, pp. 5339-5344.*
Innis et al., PCR Protocols, a guide to Methods and Applications, Academis Press (San Diego, CA (USA) 1990).
Gyllenstein, et al., Generation of single-stranded DNA by the polymerase chain reaction and its application to direct sequencing of the HLA-DQA locus, Proc. Natl. Acad. Sci., USA, vol. 85, pp. 7652-7656, Oct. 1988.
Sanchez, et al., Linear-After-The Exponential (LATE)-PCR: An advanced method of asymmetric PCR and its uses in quantitative real-time analysis, PNAS, vol. 101, pp. 1933-1938, Feb. 17, 2004.
Pierce, et al., Linear-After-The-Exponential (LATE)-PCR: Primer design criteria for high yields of specific single-stranded DNA and improved real-time detection, PNAS, vol. 102, No. 24, pp. 8609-8614, Jun. 14, 2005.
Santa Lucia, John, Jr., A unified view of polymer, dumbbell, and oligonucleotide DNA nearest-neighbor thermodynamics, Proc. Natl. Acad. Sci. USA, vol. 95, pp. 1460-1465, Feb. 1998.
Allawi, et al., Thermodynamics and NMR of Internal G-T Mismatches in DNA, Biochemistry, vol. 36, pp. 10581-10594, 1997.
Dang, et al., Oligonucleotide Inhibitors of Taq DNA Polymerase Facilitate Detection of Low Copy Number Targets by PCR, J. Mol. Biol., vol. 264, pp. 268-278, 1996.
Kainz, et al., Specificity-Enhanced Hot-Start PCR: Addition of Double-Stranded DNA Fragments Adapted to the Annealing Temperature, BioTechniques, vol. 28, No. 2, pp. 278-282, 2000.
Zuker, Michael, Mfold web server for nucleic acid folding and hybridization prediction, Nucleic Acids Research, vol. 31, No. 13, pp. 3406-3415, 2003.
Lawyer, et al., High-level Expression, Purification, and Enzymatic Characterization of Full-length Thermus aquaticus DNA Polymerase and a Truncated Form Deficient in 5' to 3' Exonuclease Activity, PCR Methods and Applications, vol. 2, pp. 275-287, 1993.
Kaiser, et al., A Comparison of Eubacterial and Archaeal Structure-specific 5'-Exonucleases, vol. 274, No. 30, pp. 21387-21394, 1999.

\* cited by examiner

*Primary Examiner*—Young J Kim
(74) *Attorney, Agent, or Firm*—Foley & Lardner LLP

(57) ABSTRACT

An additive for preventing mispriming in polymerase chain reaction (PCR) amplifications and assays comprising a hairpin oligonucleotide having a stem duplex greater than six nucleotides in length and a stabilized stem terminus. The additive improves PCR amplifications, including LATE-PCR amplifications when added to initial amplification reaction mixtures. It can be included in oligonucleotide sets and in kits for PCR amplification and assays.

19 Claims, 18 Drawing Sheets

REAGENTS AND METHODS FOR IMPROVING REPRODUCIBILITY AND REDUCING MISPRIMING IN PCR AMPLIFICATION

This application claims the benefit of U.S. Provisional Application No. 60/619,670, filed Oct. 18, 2004.

TECHNICAL FIELD

This invention relates to nucleic acid amplification reactions and assays utilizing the polymerase chain reaction (PCR), including homogeneous assays, both real-time and end-point.

BACKGROUND

Nucleic acid amplification employing the polymerase chain reaction (PCR) is well known, as are assays that include PCR amplification. See U.S. Pat. Nos. 4,683,202, 4,683,195 and 4,965,188, and, generally, PCR PROTOCOLS, a guide to Methods and Applications, Innis et al. eds., Academic Press (San Diego, Calif. (USA) 1990). Homogeneous PCR assays that do not require washing to remove unbound detector reagents or probes and thus can be performed without opening amplification reaction vessels are also well known. Homogeneous PCR assays include both end-point assays, in which amplified product is detected at the end of the amplification reaction, and real-time assays, in which amplified product is detected during some or all of the thermal cycles as the reaction proceeds. See U.S. Pat. Nos. 5,994,056, 5,487,972, 5,925,517 and 6,150,097.

PCR amplification reactions generally are designed to be symmetric, that is, to make double-stranded amplicons by utilizing a forward primer and a reverse primer that are "matched"; that is, they have melting temperatures that are as close as possible, and they are added to the reaction in equimolar concentrations. A technique that has found limited use for making single-stranded DNA directly in a PCR reaction is "asymmetric PCR." Gyllensten and Erlich, "Generation of Single-Stranded DNA by the Polymerase Chain Reaction and Its Application to Direct Sequencing of the HLA-DQA Locus," Proc. Natl. Acad. Sci. (USA) 85: 7652-7656 (1988); and U.S. Pat. No. 5,066,584. Asymmetric PCR differs from symmetric PCR in that one of the primers is added in limiting amount, typically 1-20 percent of the concentration of the other primer.

More recently we have developed a non-symmetric PCR amplification method known as "Linear-After-The-Exponential" PCR or, for short, "LATE-PCR." See Sanchez et al. (2004) PNAS 101: 1933-1938, Pierce et al. (2005) PNAS 102: 8609-8614, and published international patent application WO 03/054233 (3 Jul. 2003), which is incorporated herein by reference in its entirety. LATE-PCR takes into account the actual melting temperatures of PCR primers at the start of amplification, referred to as $T_{m[0]}$. $T_{m[0]}$ can be determined empirically, as is necessary when non-natural nucleotides are used, or calculated according to the "nearest neighbor" method (Santa Lucia, J. (1998) PNAS (USA) 95: 1460-1465; and Allawi, H. T. and Santa Lucia, J. (1997) Biochem. 36: 10581-10594) using a salt concentration adjustment. In our work we have utilized 0.07M monovalent salt concentration.

An undesirable feature of PCR amplifications, reduced in the case of LATE-PCR, is scatter among replicates. Following the exponential phase of the amplification, replicate amplifications followed in real time diverge and plateau at different levels. Scatter indicates that replicates do not have the same reaction kinetics and reduces accuracy. This is a problem for PCR assays generally, but particularly for end-point assays and assays that depend upon the slope of signal during the linear phase.

Another significant problem with PCR amplifications is mispriming, which we believe is manifest in at least three types: Type 1, mispriming that occurs during preparation of reaction mixtures prior to the start of amplification; Type 2, mispriming that occurs during amplification if cycle temperatures include any temperature significantly below the melting temperature of a primer; and Type 3, mispriming that occurs in the late stages of a PCR amplification that is continued after a high concentration of amplicon has been made. Several approaches have been used to address the first type of mispriming. One approach is to modify the polymerase chemically so that it is inactive until heated to a high temperature such as 95° C. See U.S. Pat. Nos. 5,677,152 and 5,773,258. Another approach is to bind an antibody to the polymerase to inhibit the polymerase until the reaction is heated to a high temperature such as 95° C. to irreversibly denature the antibody. See U.S. Pat. No. 5,338,671. Yet another approach is to include an aptamer in the reaction mixture. See Doug and Jayasena (1996), J. Mol. Biol. 264: 268-278 and U.S. Pat. No. 6,020,130. An aptamer is a single-stranded oligonucleotide approximately 30 nucleotides in length that binds to a polymerase and inhibits its ability to extend a recessed 3' end at low temperatures. Aptamers are not irreversibly denatured at 95° C., a typical highest temperature for a PCR cycle. Kainz et al. (2000) Biotechniques 28: 278-282 reported that the addition to PCR reaction mixtures of double-stranded DNA fragments having lengths of 16-21 nucleotides in certain amounts inhibit polymerases at temperatures below typical PCR extension temperatures and suppress synthesis of non-specific products. DNA fragments are not irreversibly denatured during PCR cycling. Eppendorf-5 Prime, Inc. markets a proprietary ligand that is said to bind to Taq polymerase in a temperature-dependent manner and to inhibit its binding to double-stranded DNA at temperatures below about 50° C. Despite these many attempts, mispriming remains a problem with PCR amplifications.

Another manifestation of mispriming during PCR amplification is known as primer-dimer formation and amplification. According to this phenomenon one primer hybridizes to the other primer or to itself and then undergoes extension of the 3' end to generate a small double-stranded amplicon, which can then amplify further or can multimerize and amplify further. Primer-dimer formation can occur in the absence of target.

Quantitative analysis of PCR amplifications has been enabled by real-time detection methods, as the PCR cycle at which fluorescent signal becomes visible above the threshold cycle or $C_T$ of reactions is indicative of starting target concentrations. End-point analyses are semi-quantitative at best, due in part to scatter among replicates as the reaction exits exponential amplification. Electrophoretic analysis of double-stranded amplicons is semi-quantitative, and may utilize fluorescently labeled primers. End-point analysis utilizing fluorescently labeled probes, either allele-discriminating probes or mismatch-tolerant probes, are also semi-quantitative at best. By reducing scatter and producing single-stranded product, LATE-PCR offers significant improvement in end-point analysis, but scatter among replicates is often not completely eliminated, leaving quantitative multiplex detection less accurate than desired.

An aspect of this invention is a class of reagent additives to improve product specificity and to eliminate the effects of mispriming in PCR amplification reactions. These additives out-perform existing "hot-start" methodologies in all types of PCR and can be used to prevent the accumulation of undesired products, including primer-dimers and misprimed amplicons, both at early stages of the reaction and during LATE-PCR reactions having many cycles (typically 60 cycles and more).

Another aspect of this invention is PCR amplification and assay methods, both symmetric PCR or non-symmetric PCR, including but not limited to LATE-PCR, and kits, partial kits, and oligonucleotide sets that include such reagent additives.

SUMMARY

Reagents according to this invention are additives that are capable of preventing one or more manifestations of mispriming in at least some PCR amplifications. By "prevent a manifestation" we mean that a product or products of mispriming are not detected at the end of a reaction by techniques described herein, namely fluorescent DNA dye, gel electrophoresis, DNA sequencing and melting-point analysis. Reagents according to this invention may be included in PCR amplification mixtures prior to the start of amplification at relatively low concentration, less than 1 micromolar (μM), that is, 1000 nM, preferably not more than 650 nanomolar (nM), more preferably not more than 300 nM, and most preferably 50-250 nM, even when utilizing polymerases that have both polymerization activity and 5'- to -3' exonuclease activity. Reagents according to this invention are modified single-stranded oligonucleotides. Oligonucleotides that may be utilized to construct reagents according to this invention are oligonucleotides broadly. They may be DNA, RNA or mixed DNA-RNA. They may contain modified nucleotides, non-natural nucleotides, for example, 2'O-methyl ribonucleotides, non-natural internucleotide linkages, non-nucleotide linkers, PNA, LNA and added chemical moieties such as capped nucleotides described by Glenn Research.

Reagents according to this invention are single-stranded oligonucleotides that form a stem-and-loop structure, commonly referred to as a "hairpin" structure, in a PCR amplification reaction mixture, although they can also be comprised of a stem-and-loop structure wherein the loop is not comprised of nucleotides. In such a structure, a central portion of the molecule remains single-stranded (not hybridized) (the loop) and the ends hybridize to one another to form the stem. A stem may be blunt ended or one strand may extend beyond the end of the other. A stem may comprise a continuous double-stranded region, or it may include an internal mismatch, causing a bulge. The end of the stem formed by the termini of the oligonucleotide is stabilized so as to be more tightly bound than a DNA-DNA hybrid. We characterize the stem of a reagent according to this invention by reference to its melting temperature, or $T_m$. The melting temperature is that temperature in degrees centigrade at which 50% of the complementary sequences of the stem are not-hybridized (open configuration) and 50% of the complementary sequences are hybridized or partially hybridized to self (closed configuration). In this application the "calculated $T_m$" of a stem means the calculated melting temperature of the stem portion of the corresponding, unstabilized complete DNA oligonucleotide obtained using the M-fold program: Zucker, M. (2003). "Mfold Web Server for Nucleic Acid Folding and Hybridization Prediction." Nucl. Acids Res. 31: 3406-3415, assuming a sodium concentration of 70 millimolar (mM) and a magnesium concentration of 3 mM. In the case of preferred embodiments that have added quencher pairs, preferably non-fluorescent quenchers such as Dabcyl and Black Hole Quenchers that absorb light but emit absorbed energy as heat, $T_m$ is the calculated $T_m$ of the DNA hairpin without the quenchers. In the case of embodiments that have capped nucleotides at their termini, $T_m$ is the calculated $T_m$ of the DNA hairpin containing the equivalent uncapped nucleotides. In the case of 2'-O-methyl ribonucleotide inclusions at a stem end, $T_m$ is the calculated $T_m$ of the all-DNA hairpin containing deoxyribonucleotide analogs of the 2'-O-methyl ribonucleotides. We utilize this methodology for the practical reason that it is difficult to obtain the actual melting point of a stabilized hairpin, recognizing that the actual melting point will be several degrees higher than the calculated $T_m$ due to the stabilizing modification. Reagents according to this invention have a calculated stem $T_m$ that does not exceed 94° C., and preferably is in the range of 50-85° C. For some embodiments we prefer a calculated stem $T_m$ that is higher than the primer annealing temperature (typically 55-72° C. of an amplification reaction, that is, in the range of 72-85° C.), but in other embodiments we prefer a calculated stem $T_m$ that is lower than the primer annealing temperature, that is, in the range of 50-71° C. The complementary sequences of the stem open, become single-stranded, at 95° C., the temperature used for the strand-melting during PCR cycling. Further, the stem of reagents according to this invention has a length exceeding six nucleotides at temperatures low enough for formation of a closed, self hybridized, confirmation. Currently our preferred embodiments form stems that are 9-12 base pairs long, preferably 9-11 base pairs, when closed, more preferably 9-12, most preferably 9-11, continuous complementary base pairs without internal mismatches, most preferably blunt-ended stems that are 9-12 base pairs long and perfectly complementary. The 3' terminus of the reagent is non-extendable by a DNA polymerase in the amplification reaction, so the reaction is not a PCR primer. Any overhanging 3' end is blocked to prevent extension, for example, by adding a phosphate or some blocking chemical moiety.

The length of the loop can be varied considerably. If a loop consists of nucleotides and inter-nucleotide linkages, it is at least three nucleotides in length. Further, if it is just three nucleotides long, it contains a thymidine residue. Our currently preferred nucleotide loops have lengths in the range of 3-22 nucleotides. Loops may also be non-nucleotide chemical linkers, for example, alkylene chains. For carbon-chain linkers we prefer a length of 3-6 carbon atoms, and a most preferred length of 3 carbon atoms. In alkylene carbon chains the remaining two valence electrons of each member of the carbon chain are also engaged in covalent linkages. Such linkages can be to hydrogen atoms, to short-chain alkyl or alkylene groups, to substituents for linking the reagent to a solid surface. Non-oligonucleotide loops comprising chemical linkers are not limited to hydrocarbon chains and may include hetero (not carbon or hydrogen) atoms. We prefer that chemical linkers be electrically neutral so as not to bind to the polymerase. Because the activity of the reagent depends on the closed confirmation of the stem, it is preferred that the composition of the loop, for reagents having loops of more than 5 nucleotides, not be extensively complementarity to any other sequence or sequences in the reaction, or generated by the reaction. A reagent according to this invention is not a hybridization probe for any product of the amplification reaction and does not signal product accumulation.

As indicated, reagents according to this invention include stabilization of the end of the stem remote from the loop such that the end of the stem is more tightly bound than the end of a DNA-DNA hybrid. In our currently most preferred embodiments, the stem is blunt ended, and the terminus of the stem is modified in a manner that inhibits partial strand separation compared to a natural DNA-DNA hybrid. We demonstrate below the effect of adding stabilizing interactive chemical moieties to the ends of the stem, both a pair of Dabcyl moieties covalently attached to the 3' and 5' nucleotides of the stem by means of a commercial linker and a pair of commercially available Black Hole™ quenchers (proprietary quenchers marketed by Biosearch Technologies, Novato, Calif., U.S.A.). We also demonstrate the effect of utilizing strongly binding non-natural nucleotides, 2' O-methyl ribonucleotides, at the end of the stem. Preferred stabilizing moieties are non-fluorescent so that the reagents do not contribute background fluorescence to amplifications and amplification assays. Unstabilized oligonucleotide DNA hairpins of reagents according to this invention, added at concentrations below 1 µM, need not substantially reduce mispriming if not modified as described to stabilize the hydrogen-bonded stem terminus, and in many cases do not do so. Thus, stabilization is essential in reagents according to this invention.

Hairpin reagents according to this invention may be described as molecules that contain two complementary nucleotide oligomeres that are held together such that they can form a stem of greater than 6 base pairs, and the open end of the stem is chemically modified by one means or another such that the tendency of the stem to unwind or "fray" at its open end is suppressed. Although a thorough understanding of the molecular mechanism of action awaits further analysis via enzyme kinetics in the presence and absence of reagents according to this invention, as well as structural analysis of the interaction of such reagents with the polymerase via electron microscopy, nuclear magnetic resonance, and X-ray crystallography, a partial understanding of mechanism can be anticipated based on the information presented here and in the scientific literature. The literature teaches that Taq polymerase, like other DNA polymerases, is comprised of a synthetic domain and a 5'exonucleolytic domain. The 5'exonucleolytic domain is not present in the Stoffel fragment. The literature further teaches that the synthetic domain carries out DNA polymerization by first binding to and sliding along double stranded DNA. The synthetic domain has a shape that has been likened to an "open hand" which, in the presence of dNTP's, undergoes a shape change at the polypeptide level upon contact with double stranded DNA. As a result the "fingers" of the "hand" "close" around the double stranded DNA molecule. Mismatched sequences within a double-stranded molecule cause the polymerase to back up for some nucleotides and substitute the correct base using the 3'editor function of the synthetic domain. Synthesis of a new DNA strand occurs as the enzyme reads the template strand and extends the 3' end of the complementary primer. If the enzyme encounters a 5' tail of an oligonucleotide already bound to the template strand the polymerase can invade the region of the bound oligonucleotide by 1-2 nucleotides and cleave the resulting 5' tail by means of the 5'exonuclease domain of the enzyme.

Based on this information it can be hypothesized that the double-stranded stem of a reagent according to this invention functions, at least in part, by binding to the synthetic domain of the polymerase in the open conformation and causing it to close. The synthetic activity of the polymerase is thereby inhibited. Thus, while not wishing to be bound by any theory, it can be postulated that the First Mode of action is as a temperature-dependent inhibitor of the synthetic activity of the polymerase. The evidence presented below indicates that at least some versions of the reagents are not released by the enzyme at the melting temperature of their double-stranded regions, e.g., stems, but remain bound at higher temperatures, including especially typical PCR extension temperatures. During the denaturation (or strand-melting) step of a PCR cycle, however, reagents of this invention become unbound from DNA polymerase. During the denaturing step of PCR cycles (also referred to as the strand-melting step), typically above 90° C., the stems of hairpin reagents according to this invention melt apart, and they bind again to the polymerase only if and when the temperature is dropped sufficiently for the double-stranded region to reform. Therefore, one may choose to design a reagent according to this invention that is double-stranded only until the first denaturation, that is, is double-stranded when added to a PCR reaction mixture prior to amplification (commonly at room temperature) but is thereafter maintained above the $T_m$ of its stem. For such an embodiment the primer annealing temperature of all amplification cycles and any LATE-PCR low-temperature detection temperature are higher than the calculated stem $T_m$, preferably by at least 5° C. Alternatively, one may choose to design a reagent according to this invention that again becomes double-stranded later during amplification. This can be accomplished by utilizing a stem $T_m$ (calculated as described) that is higher than the primer annealing temperature used in all or some amplification cycles. Alternatively, in LATE-PCR amplification, this can be accomplished by utilizing a stem $T_m$ that is below the primer—annealing temperature but higher than a low-temperature detection temperature. The former design type generally will not inhibit polymerization, as indicated by a delay in $C_T$, whereas utilizing a primer annealing temperature below the stem $T_m$ generally will result in a modest delay of the $C_T$ of 1-3 amplification cycles.

Further, while not wishing to be bound by any theory, it can be postulated that a Second Mode of action of reagents according to this invention is as a temperature-dependent inhibitor of the 5'exonucleolytic activity of the polymerase. We show below that reagents according to this invention inhibit the 5'- to -3' exonuclease activity of the polymerase enzyme at temperatures up to at least 55° C. and do so without unduly suppressing the capacity of the enzyme to extend a DNA strand by polymerization of its 3' end (as PCR primers are extended in PCR amplifications).

In addition, while not wishing to be bound by any theory, it can be postulated that a Third Mode of action of reagents according to this invention is as a temperature-dependent ligand that binds the polymerase causing the polypeptides of the polymerase to change shape. Once the ligand is released from the enzyme, the enzyme remains in the altered shape for some time before returning to its former shape. While in the altered shape the enzyme preferentially binds to completely complementary primer-template hybrids, as compared to partial mismatched primer-template hybrids.

Based on this model it can be anticipated that the capacity of the stem of reagents according to this invention to change the shape of the synthetic domain of the polymerase is different from the capacity of reagents according to this invention to inhibit either the synthetic function of the polymerase (First Mode, above) or the 5'exonuclease function of the polymerase (Second Mode, above). Both the First Mode and the Second Mode of action actually depend on the rate at which the bound reagent is released by the polymerase. Reagents according to this invention which are released rapidly preferentially act by the Third Mode without significantly inhibiting the synthetic activity of the polymerase, even at high concentration. In contrast, reagents according to this invention which are released from the polymerase slowly are likely to be inhibitory at high concentration. By way of example, neither compound 12-C3DD comprised of a stem and a carbon-linker loop of three methylene (—$CH_2$—) groups, nor compound 12-C3 C3DD comprised of a stem and a carbon-linker loop of six methylene (—$CH_2$—) groups only partially inhibit PCR amplification at concentrations of 3000 nM. In contrast, reagents according to this invention having loops comprised of nucleotides typically inhibit PCR amplification completely a concentration of <1000 nM and sometimes at concentrations less than <500 nM in the assay of Example 1.

As persons familiar with protein-nucleic acid interactions will appreciate, the action of a reagent according to this invention may be by more than one of Modes 1-3, which are not mutually exclusive, but rather are relative. As described below, we have devised a quantitative test (Example 14) that can be used to determine the extent to which a particular molecular structure linking the two oligonucleotides comprising the stem causes the complete compound to act as an enzyme inhibitor (via the First Mode or the Second Mode) or primarily as an enhancer of enzyme specificity, the Third Mode of action.

Based on the above model it can be further anticipated that one or more polymerase molecules can be bound to an equal number of molecules of a reagent according to this invention, which, in turn, are covalently linked to a larger moiety such as bead, particle, or material made of a solid material. The solid could thereby be considered to be "loaded" with polymerase. The linkage of reagents according to this invention to the solid could be temporary or could be cleavable by a variety of means known in the art. Cleavage of the linkage would release the reagent or the reagent-polymerase complex into solution (subsequently the reagent could be released from the polymerase).

Design of reagents according to this invention is within the skill of the art. It will be appreciated that the melting temperature of a stem can be adjusted considerably by varying its G-C content. For example, stems of two preferred embodiments described below both have a length of nine nucleotides, but they have calculated $T_m$'s that differ by 25° C. (81° C. and 56° C.). We commonly use the M-fold computer software program cited above for calculation of stem $T_m$, in conjunction with one or more possible loop sequences. Loop sequence has not otherwise been found to be significant in mispriming reagents according to this invention. In our designing, we utilize a sequence that forms a perfect blunt-ended stem, that is, a stem with no internal mismatches and no terminal overhang. One could then, by simple trial, evaluate the effect of introducing an internal mismatch (a terminal mismatch is destabilizing and not acceptable, as shown in Example 1) or a short extension of one or, at most, two nucleotides beyond the double-stranded region.

Construction of reagents according to this invention is within the skill of the art. For example, oligonucleotide sequences can be prepared on an oligonucleotide synthesizer. Stabilizing moieties can be included using known methods. For example, Dabcyl's can be added conveniently by starting with a dabcylated column (Glen Research) and concluding synthesis with a Dabcyl-modified nucleotide. Non-natural nucleotides can be used as the first, and penultimate, and last nucleotides of the synthesis.

Once a candidate reagent is designed and constructed, the melting temperature of its stem can be approximated empirically in some cases by adding fluorescent DNA-binding dye and performing a melt analysis while stimulating the dye (recognizing that the dye itself has an effect on $T_m$). Also, practical useful information regarding the actual melting temperature of a stabilized stem of a reagent according to this invention can in many cases be obtained inferentially by performing real-time PCR amplifications utilizing different annealing temperatures. Adjustments in stem length or G-C content may be made, if needed, to achieve a desired $T_m$. We then evaluate the effects of a candidate reagent on various manifestations of mispriming and amplification efficiency by determining its performance in a rigorous PCR amplification such as described below in Example 1. A candidate reagent is judged to be a reagent according to this invention if, when included in the reaction mixture of Example 1 at some concentration below 1000 nM, preferably not more than 650 nM, a clean amplicon is obtained (See FIG. 1). We evaluate candidate assays using the assay of Example 1 except with the intended target and intended primers. However, amplifications and assays (amplification plus detection) according to this invention are not limited to the conditions or procedures of Example 1. While a reagent according to this invention must inhibit at least one manifestation of mispriming when added at a concentration below 1000 nM compared to a polymerase concentration (Example 1) of 1.25 units per 25 µl of reaction mixture, the reagent can be used at any concentration relative to the polymerase concentration at which it is effective; that is, any concentration (or relative concentration) at which it prevents mispriming but does not substantially prevent amplification. Utilizing the intended primers in the evaluation will reveal unintended consequences, such as failure to block the 3' end of the reagent or an overlooked complementarity.

This invention includes PCR amplification reactions and assays that include PCR amplification reactions, including reactions wherein the amplification reaction mixture includes a thermostable DNA polymerase having both polymerization activity and 5'-3' exonuclease activity, such as Taq DNA polymerase, and wherein at least one reagent according to this invention is included in the amplification reaction mixture. Many reagents according to this invention inhibit the activity of the polymerase and are added at a concentration relative to the polymerase concentration within the ranges described above prior to or during thermal cycling that is, not more than 1000 nM, preferably not more than 650 nM for a reaction containing 1.25 units of DNA polymerase per 25 µl of reaction volume. Some reagents according to this invention, while effective at concentrations below 1000 nM and preferably at concentrations below 650 nM, inhibit the activity of the polymerase to a lesser degree and can be added at concentrations up to 1500 mM or even 3000 nM for such a polymerase concentration. In assays containing more than one reagent according to this invention, each reagent can have a stem with its own $T_m$ and can be added at its own concentration, such that different reagents function in different portions of the steps in the amplification process. If a reagent of this invention is added during thermal cycling, it should be added without aspirating the reaction mixture into the work area. Such amplification reactions include symmetric PCR amplifications, asymmetric PCR amplifications and LATE-PCR amplifications, any of which may further include reverse transcription, if RNA targets are involved. PCR amplifications may be used to prepare amplified product for any purpose, for example, as a starting material for dideoxy sequencing. PCR amplifications may be combined with detection of amplified product in an assay, including particularly homogeneous assays employing labeled primers, labeled probes or fluorescent DNA-binding dyes such as SYBR Green or ethidium bromide. The assay can be a real-time assay in which detection readings are taken during multiple amplification cycles or an end-point assay in which detection is performed after the completion of amplification. It may be qualitative or quantitative, including but not limited to a quantitative end-point assay. The assay can be designed to amplify a single double-stranded or single-stranded product, or more than one double-stranded products without or with related single-stranded products.

As used in this application, "LATE-PCR" means a non-symmetric DNA amplification employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon, wherein the concentration-adjusted melting temperature of the Limiting Primer at the start of amplification, $T_{m[0]}$, is higher than or not more than 5° C. below the concentration-adjusted melting temperature of the Excess Primer at the start of amplification, $T_{m[0]}^X$, preferably 3-10° C. higher; and wherein thermal cycling is continued for multiple cycles after exhaustion of the Limiting Primer to produce single-stranded product, namely, the extension product of the Excess Primer. LATE-PCR assays may include a low temperature detection step in which the temperature is reduced below the primer annealing temperature during at least some cycles of linear amplification. Preferably such a step occurs following extension before strand melting.

This invention also includes complete PCR kits, partial kits, and oligonucleotide sets. A complete PCR amplification kit includes at least all the reagents for carrying out a PCR amplification or assay, including at least one pair of PCR primers, dNTP's, reaction buffer, thermostable DNA polymerase, preferably a polymerase having 5'- to -3' exonuclease activity, and at least one reagent according to this invention. A complete kit for a homogeneous PCR assay further includes any additional detection reagents that are needed, for example, a fluorescent DNA dye or fluorescently labeled probes. A complete kit of either type preferably includes reagents for sample preparation and may include, in some embodiments, a reverse transcriptase. Partial kits according to this invention omit at least some ingredients of a complete kit but include at least the thermostable DNA polymerase (and, if needed, reverse transcriptase) and at least one reagent according to this invention. For example, products known commercially as "master mix" or "basic kit" typically omit PCR primers and probes. A preferred partial kit includes all reagents needed for an amplification or assay except for sample preparation. Oligonucleotide sets according to this invention include at least one pair of PCR primers and at least one reagent according to this invention. They may further include oligonucleotide probes or sequencing primers.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
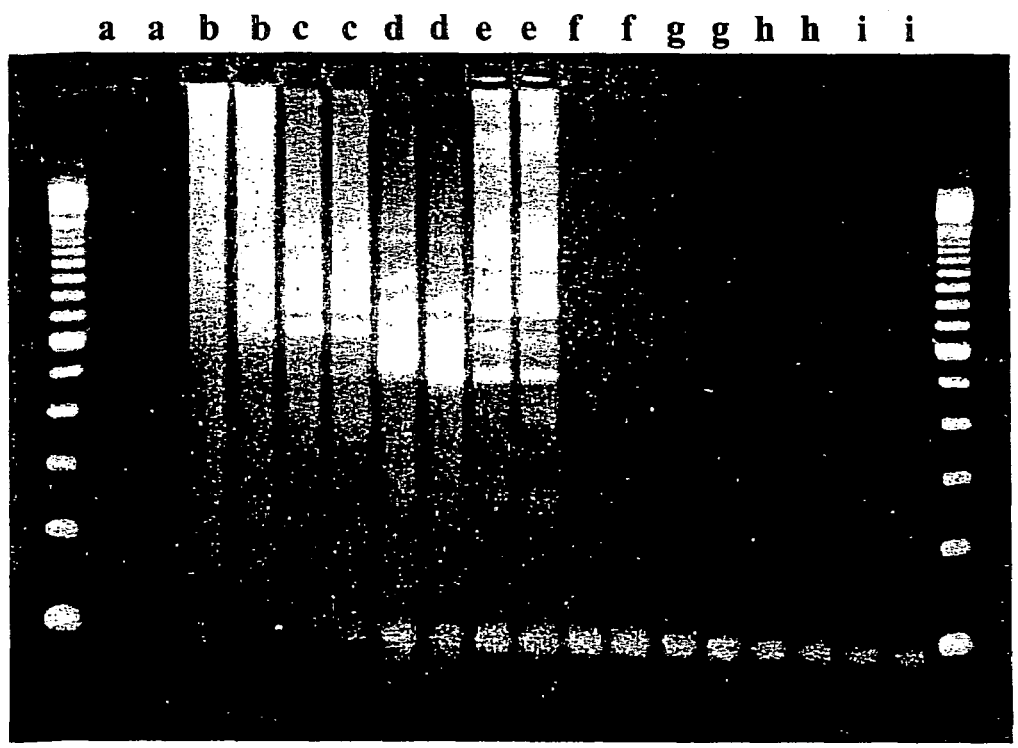
FIG. 1 shows a gel electrophoresis analysis of samples from a qualitative rigorous PCR assay for mispriming errors designed to test the inhibitory activity of the reagents described in this invention.

As indicated above, we have identified what we believe to be three different types and causes of mispriming errors. To assess mispriming of all three types we have developed the rigorous assay of Example 1 below. Amplification begins with sheared DNA, which promotes mispriming. Physical handling, for example, drawing DNA into a pipette, tends to shear DNA. Further, because only Type 1 mispriming can be prevented by "hot start" reagents and methods, we have included in the assay many temperature cycles (at least 60). In addition we have included a low-temperature detection step utilized in some LATE-PCR assays. Further, we also recognize formation of primer-dimers and their further oligomerization and amplification as an additional type of mispriming. Primer-dimer formation and amplification can occur both in the presence and absence of added template DNAs, and we have also developed assays for these phenomena.

Whereas hot-start enzymes are effective only prior to the start of amplification due to irreversible changes that occur upon heating to high temperature, for example, 95° C., mispriming reagents according to this invention, are not irreversibly denatured and could have positive or negative effects, or both, later in the reaction, if a low temperature step is included.

One can design stems to have melting temperatures, $T_m$'s, above or below particular cycle temperatures, with different impacts on amplification. In designing stems one preferably takes into account that melting is a dynamic phenomenon occurring over a temperature range, with $T_m$ specifying the temperature at which fifty percent of molecules are in double-stranded form and fifty percent are in single-stranded form. We believe that the binding of some closed stems to polymerase shifts the equilibrium among molecules that remain unbound to polymerase in favor of more stems closing. If we wish the vast majority of stems to be closed at a particular cycle temperature, such as the primer annealing temperature, we generally start with an unmodified oligonucleotide stem having a calculated $T_m$ at least 5° C. above that temperature, recognizing that stabilizing stem modification will raise the actual $T_m$ by several degrees. Conversely, if we wish the vast majority of stems to be open at a particular cycle temperature, we generally start with an unmodified oligonucleotide stem having a calculated $T_m$ of at least 5° C. below, preferably at least about 10° C. below, that particular cycle temperature, again recognizing that stabilizing stem modification likely will raise the actual $T_m$ by several degrees.

Utilizing a particular reagent according to this invention with differing primer annealing temperatures can have differing effects on amplification efficiency, as we demonstrate below in Example 5. One of our currently calculated embodiments (compound 9-22 DD) discussed below has a calculated $T_m$ of 81° C. It will close during every typical PCR thermal cycle as the temperature is lowered from the strand-melting temperature (for example, 95° C.) to the primer annealing temperature (for example, 55° C.). A reagent with such a stem will have an effect during each cycle of amplification. Another of our currently preferred embodiments (compound 9-3 DD) has a calculated $T_m$ of 56° C. When PCR amplification mixtures are prepared at room temperature, this reagent has a closed stem and binds to the polymerase. It remains bound as the temperature is raised at the commencement of amplification. Polymerase-bound molecules of 9-3DD become unbound and open during the initial high-temperature step, and do not bind to the polymerase again unless the temperature is lowered sufficiently for the stem of the unbound molecules to close. Thus, by keeping the lowest cycle temperature at 65° C., the stem does not reform. Under these conditions this embodiment will function in that amplification as a hot-start reagent to prevent mispriming that occurs prior to the start of amplification. However, if a low-temperature detection step is included, for example 40° C. incubation following extension in a LATE-PCR cycle to permit hybridization of a low-temperature molecular beacon or other labeled probe to the single-strand accumulating during the linear phase of amplification, the stem having a calculated melting temperature of 56° C. stem will close, permitting the reagent to bind to the polymerase again until a high-temperature of strand melting is achieved.

Example 1 below describes a rigorous LATE-PCR assay that we utilize to evaluate the performance of reagents according to this invention. FIG. 1 shows that mispriming errors occur not only with "regular" Taq DNA polymerases, that is, thermostable DNA polymerases with 5'- to -3' exonuclease activity but without hot-start modification (lanes b and lanes c), but also with hot-start Taq polymerases (lanes d and lanes e). FIG. 1 further shows the elimination of non-specific products formed due to mispriming errors, and the presence of only the desired specific product, obtained by the addition of reagent 9-22 DD at 300 nM concentration, not only to amplifications with hot-start polymerases (lanes h and lanes i), but also to amplifications with regular Taq DNA polymerases (lanes f and lanes g). The effectiveness of compounds 9-22 DD and 9-3 DD in suppressing mispriming was assessed utilizing the assay described in Example 1. Both were found to suppress Type 1 mispriming. The low calculated $T_m$ of the stem of 9-3 DD (56° C.) permits it to be used as simply an effective hot-start reagent by utilizing a PCR amplification protocol with all cycle temperatures 60° C. and above. By staying above the stem's melting point the stem does not reform as amplification proceeds. Compound 9-3 DD has no inhibitory effect on polymerization efficiency when so used. Example 5 below is instructive in this regard. It compares amplifications utilizing reagent 9-3 DD and annealing temperatures of 65° C. and 55° C. When 65° C. was utilized, no effect on polymerization efficiency, as reflected by the $C_T$, was found. When 55° C. was utilized, however, the $C_T$ was delayed. This is evidence that if the temperature is lowered sufficiently for the stem to close and the polymerase to be engaged, engagement continues as the temperature is raised for primer extension, even if the primer extension temperature is above the stem $T_m$. On the other hand, the high $T_m$ of the stem of 9-22 DD (81° C.) permits the stem to reform into a hairpin during the primer annealing step of every PCR cycle. It prevents the manifestation not only Type 1 mispriming, but also Type 2 mispriming, Type 3 mispriming, and Primer-Dimer formation. It does affect polymerization efficiency somewhat, however, as evidenced by a 1.5 cycle delay in the threshold cycle ($C_T$) of the PCR amplification followed in real time with SYBR Green 1 or a target-specific molecular beacon probe when used at a 100 nM concentration.

Table I in Example 1 reports the application of that rigorous assay to a series of additives, and further reports the minimum concentration needed to achieve prevention of manifestations of mispriming, that is, the avoidance of detectable levels of non-specific products formed due to mispriming errors, and the presence of only the desired specific amplification product such as is shown in lanes f and g of FIG. 1, using regular Taq DNA polymerase rather than a hot-start version. In Table I compounds are identified by our nomenclature system. Unmodified hairpin molecules are identified by the stem loop length. For example, compound 6-22 has a stem six nucleotides long and a loop twenty-two nucleotides long. Because the loop identifier begins with a number or is only a number ("22" or "3b") the loop is nucleotides. Non-nucleotide loops are specified further. Compound 12-C3C3 has a stem twelve nucleotides long and a loop that is a six-carbon chain, that is, a chain of six methylene (CH2) groups. Various modifications were made to one or both ends of the basic hairpins. These are designated by suffixes, where 3D is a Dabcyl (5'-Dimethoxytrityloxy-5-[(N-4'-carboxy-4-(dimethylamino)-azobenzene)-aminohexyl-3-acrylimido]-2'-deoxyUridine-3'-[(2-cyanoethyl)-(N,N-diisopropyl)]-phosphoramidite) added to the 3' terminal nucleotide, 5D is a Dabcyl added to the 5' terminal nucleotide, DD is a Dabcyl added to both terminal nucleotides, BHQBHQ is a Black Hole Quencher added to both terminal nucleotides, FF is a fluorophore (in this case FAM) added to both terminal nucleotides, AA is an adenosine (A) added to both terminal nucleotides, and TT is a thymidine (T) added to both terminal nucleotides.

As well as additions, several modifications were made to the basic stems. The suffix 2'OM$^4$ indicates that four terminal nucleotides, the last two on each stem oligonucleotide, or arm, were changed from deoxyribonucleotides to 2'-O-Methyl nucleotides. To change the melting temperature of stems, we changed the G-C content. Compounds in which the stem sequence, but not the stem length, was changed are denoted by a lower-case letter designator preceding the terminal-modifier suffix, for example, 9-3b DD or 9-3i DD. The nucleotide sequences, showing also carbon-chain loops were used, for the various compounds in Table I are presented in Table II. Table I is instructive in several regards. It shows, for example, that in that assay unmodified DNA hairpin oligonucleotides either are not effective or are effective only at high concentrations, 1000 nM or higher. Oligomer 9-22 (stem 9 nucleotides long, loop 22 nucleotides long) was effective only at 3000 nM concentration, the amount reported for mispriming suppression by double-stranded DNA. Oligomers 6-22 (stem 6 nucleotides long, loop 22 nucleotides long) and 9-5 (stem 9 nucleotides long, loop 5 nucleotides long) were not effective even at 3000 nM concentration. However, when the 9-22 oligomer was modified by adding Dabcyl moieties to both ends of the stem to create compound 9-22 DD, a preferred reagent according to this invention, only 50 nM concentration was required to prevent manifestations of mispriming. When the 9-3 oligomer was similarly modified, only 100 nM concentration was required.

Table I shows the effect of stem length. Whereas the several oligomers having stems nine and twelve nucleotides eliminated mispriming at low concentration when modified with a pair of interacting Dabcyl quenchers, oligomer 6-22 did not so respond to modification: composition 6-22 DD, not a reagent according to this invention, was effective only at high (3000 nM) concentration. Reagents according to this invention have stems longer than six nucleotides and shorter than fourteen base pairs in most cases. Lengths shorter than fourteen base pairs are currently preferred.

Table I also shows the effectiveness of other modifications that increase the binding strength at the end of the stem. Addition of a pair of interactive Black Hole™ quenchers to the stem of oligomer 9-5 produced reagent 9-5 BHQBHQ, of which only 100 nM concentration was required to yield elimination of non-specific products formed due to mispriming errors, and the presence of only the desired specific amplification product. Substitution of two 2'-O-methyl ribonucleotides at each end of oligomer 9-5 produced reagent 9-5 2'OM$^4$, for which only 50 nM concentration was required.

Table I shows that the length of the oligonucleotide loop can be varied considerably. Loop lengths of three nucleotides (reagent 9-3 DD), five nucleotides (reagent 9-5 DD), and twenty-two nucleotides (reagent 9-22 DD) all resulted in reagents according to this invention that prevented mispriming at concentrations of 100 nM or less. At the same time Table I shows that some trial and error adjustment is needed for optimization. If a pair of 2'-O-methyl ribonucleotides is substituted for the Dabcyl quenchers in the stabilizing modification of oligomer 9-5 (comparing reagent 9-5 2'OM$^4$ to reagent 9-5 DD), the level of effectiveness is unchanged: only 50 nM concentration is required. However, making the same change to modified oligomer 9-3 (comparing reagent 9-3 2'OM$^4$ to reagent 9-3 DD), the level of effectiveness, while still good, was diminished: 300 nM concentration was required rather than 50 nM concentration. The same data shows that increasing the loop length of reagent 9-3 2'OM$^4$ by two nucleotides to create reagent 9-5 2'OM$^4$ improved effectiveness: only 50 nM concentration was required rather than 300 nM concentration. Candidate reagents can be routinely evaluated and adjusted with the aid of a rigorous assay such as the one described in Example 1.

Table I also shows that compounds comprised of two complementary oligonucleotides held together in opposite polarity by a non-nucleotide bridge (loop) are also active when the free 3' and 5' ends of the oligonucleotides are modified according to this invention (in the tested embodiments by Dabcyl moieties). Table 1 shows that the size of a non-nucleotide bridge is not critical. The bridges described in Table I are chemical linkers comprised of linear chains of 3-6 carbon atoms, but many other variations on non-nucleotide bridges (loops) could be constructed by persons skilled in the art. The data in Table I suggest that a bridge of a 3 carbon-atom chain is better than one of a 6 carbon-atom chain for the same oligonucleotide stem (active at a lower concentration) and, while not rigorously tested, we hypothesize that this difference reflects the relative flexibility of the bridges and their consequent effect or ability to raise or lower the melting temperature of the stem. We utilize chemically neutral linkers (uncharged), which we prefer.

Different applications of reagents and methods according to this invention are exemplified in Examples 2-4 below. Example 2 describes the utilization of reagent 9-22 DD in a LATE-PCR assay that is a real-time assay but is shown to be suitable for an end-point assay as well. The assay of Example 2 utilizes a detection technique that is the subject of our simultaneously filed U.S. Provisional patent application No. 60/619,654 titled Primers, Probes and Methods for Nucleic Acid Amplification, which is incorporated herein by reference in its entirety. That detection technique includes adding both a fluorescent DNA dye such as SYBR Gold, which fluoresces when bound to double-stranded DNA, and a fluorophore-labeled hybridization probe complementary to single-stranded amplicon produced in a LATE-PCR amplification following exhaustion of the limiting primer, where the fluorophore is stimulated by emission from the dye; stimulating the dye; detecting emissions from both the dye and the fluorophore; and calculating the ratio of the fluorophore signal to the dye signal. Example 2 thus shows the compatibility of reagents according to this invention with fluorescent probes and fluorescent dyes, and effective prevention of mispriming when used with either or both.

Example 4 describes several multiplex LATE-PCR amplifications utilizing two, three, four and even five primer pairs, and shows amplification of the correct amplicons in all cases when reagent 9-3 DD was added to the reaction mixture. Although amplified products were analyzed by gel electrophoresis for the purpose of Example 4, the multiplex method is also applicable to multiplex assays, including qualitative and quantitative assays, such as real-time assays, employing other detection means such as fluorescent hybridization probes for intended amplicons. For real-time LATE-PCR assays, we prefer to utilize a low-temperature detection step following the step of primer extension and low temperature probes as illustrated, for example, in Example 3.

Example 13 illustrates that amplification reactions with amplification reaction mixtures containing more than one version of the reagents according to this invention can also be utilized. For instance, an amplification mixture can contain both a compound of this invention with a high melting temperature and another compound of this invention with a low melting temperature, each added at its own optimized concentration. The stem of compound 9-22DD with a calculated $T_m$ of 81° C. is in the closed conformation at the start of the reaction and soon after the temperature decreases during each thermal cycle, while compound 12-3DD with a calculated $T_m$ of 58° C. is only closed at relatively low temperatures. It therefore acts as a "hotstart" to prevent mispriming when the reaction mixture is being prepared at room temperature, but during the subsequent thermal cycles of a PCR amplification having an annealing temperature of 60° C. or higher does not close and bind to the polymerase. Mixtures of reagents are particularly useful for construction of multiplex reactions in which multiples pairs of primers spanning a range of annealing temperatures are combined for amplification of multiple amplicons. The mixture of reagents used in Example 13 is better than either single reagent alone.

Example 3 describes a LATE-PCR amplification utilizing reagent 9-3 DD to prepare amplified single-stranded product that is sufficient in amount and sufficiently free of non-specific products arising from mispriming and to be suitable for use as a starting material for sequencing. The amplification was extended to seventy cycles to insure sufficient starting material. We have found that some amplicons are more prone to Type 2 and Type 3 mispriming errors than are other amplicons. In amplifications where such mispriming is more likely, we prefer the stem of the reagent according to this invention to close when the cycling temperature drops from strand-melting step to the primer-annealing step. This can be ensured by adjusting the stem $T_m$, the annealing temperature, or both. In related work we have found that product dilution is a simple clean-up method for use with sequencing, as disclosed in our simultaneously filed U.S. Provisional patent application identified above.

We have investigated the functioning and effectiveness of embodiments of reagents of this invention as compared to unmodified DNA hairpin-forming oligomers, and one another. We devised a DNA polymerization assay to determine the extension of a labeled primer by Taq DNA polymerase in the presence of a test reagent. The assay utilizes primers that are labeled with fluorophores that are excited by emission from a fluorescent dye, as disclosed in our simultaneously filed United States Provisional patent application identified above. The assay mixture comprises 0.5 µM concentration of a synthetic oligonucleotide DNA template, 1.5 µM concentration of a DNA primer complementary to the 3' end of the template and labeled with Cy5 at its 5' end, PCR buffer, $MgCl_2$, Taq DNA polymerase, a 1:40,000 dilution of SYBR Green fluorescent DNA dye, and the test reagent.

Controlled initiation of the reaction is achieved by addition of dNTP's. The reaction is isothermal: it proceeds at a prescribed temperature for a prescribed amount of time. For evaluating the effect of the test compound on the 5'-3' exonuclease activity of the DNA polymerase, we add to the reaction mixture a "blocker", namely an oligonucleotide that is complementary to the 5' end of the template, that is blocked at its 3' end with a phosphate, and that is labeled with ROX at its 5' end. For evaluating the effect of the test compound on the polymerization activity of the DNA polymerase, the blocker is not used. To facilitate analysis of reaction products by melting-curve analysis, the template, primer and blocker are designed so that the following hybrids are readily distinguishable by their melting temperatures: primer-template, blocker-template, full-length extension product-template, and partial extension product (up to the blocker)-template. Real-time analysis is obtained by periodically exciting the dye and periodically monitoring the fluorescence emission from the dye and from the two fluorophores, both of which are excited indirectly by emission from the dye. Increase in SYBR Green I fluorescence indicates polymerization. Decrease in ROX fluorescence indicates degradation of the blocker. End-point analysis is obtained by stopping the reaction by adding 12 mM EDTA, adjusting the SYBR Green I dilution to 1:14,200, and adjusting the test compound concentration to 800 nM; and then performing a standard melting curve analysis, while stimulating the dye and monitoring fluorescence from each of the two fluorophores.

We evaluated compounds 9-22, 9-22 DD and 9-3 DD with incubations at 55° C. for 60 minutes. We also included a control with no test compound. Results from the control incubated with blocker present but no test compound indicate that Taq DNA polymerase extended the primer through the blocker region, although not completely under these conditions, producing product with nearly a single melting peak according to Cy5 fluorescence. Thus, the enzyme exhibited both polymerization activity and 5'-3' exonuclease activity. Results with compound 9-22 DD present at 300 nM concentration or 1000 nM concentration showed production of partial extension product and an effect on the amount of residual blocker in a dose-dependent manner. Thus, compound 9-22 DD inhibited the 5'-3' exonuclease activity of the polymerase at 55° C. There was a decrease in the production of full-length product, particularly at 1000 nM concentration, suggesting that at the high concentration compound 9-22 DD begins to inhibit polymerization.

Another assay that we have utilized to investigate the properties of reagents according to this invention is described below in Example 6. That assay detects the ability of a test reagent to inhibit extension by Taq DNA polymerase at 25° C. Results reported in Example 7 show that, whereas unmodified hairpin oligonucleotides 9-22 and 9-3 had no effect relative to a control, reagents 9-22 DD and 9-3 DD inhibited primer extension in a dose-dependent manner. Thus, even at a temperature sufficiently low for reagents according to this invention to inhibit polymerization activity at low concentrations, their unmodified analogs did not have that property at the same concentrations.

Figure 7:
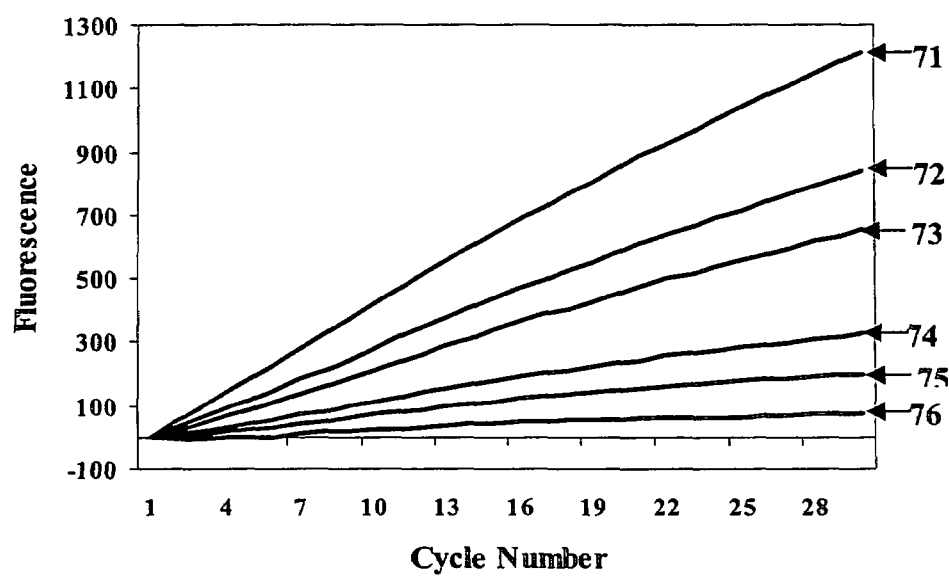
FIG. 7 illustrates an assay for assessing the effect of the reagents according to this invention on a polymerase's exonuclease activity in the absence of polymerase activity.

We have utilized two assays to investigate the inhibitory effect of reagents according to this invention on 5'-to-3' exonuclease activity of DNA polymerase. One assay is described below in Example 7. The assay measures inhibition of 5'- to -3' exonuclease activity during thermal cycling. FIG. 7 shows that reagent 9-22 DD inhibits that exonuclease activity in a dose-dependent manner at low concentrations ranging from 50 nM to 300 nM.

Figure 9:
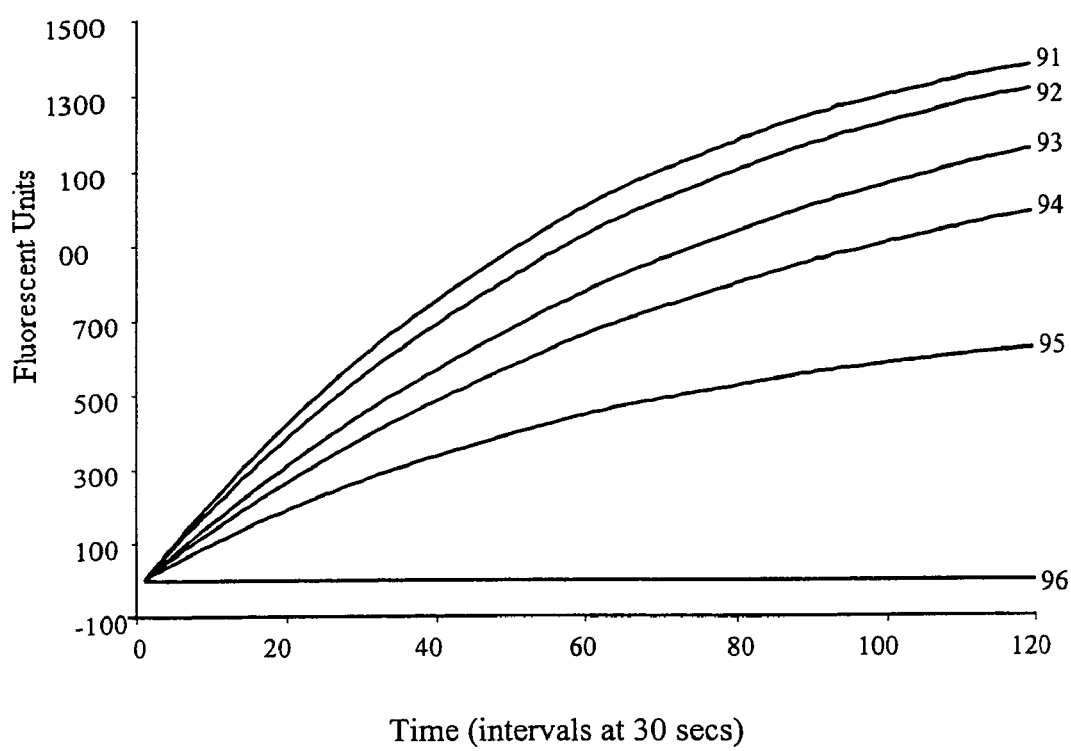
FIG. 9 illustrates an assay for quantifying exonuclease inhibition.

The second assay is described below in Example 9. It measures quantitatively the inhibition of 5'-to-3' exonuclease activity at 25° C. FIG. 9 shows dose-dependent inhibition by reagent 9-22 DD at concentrations from 50 nM to 1000 nM.

Yet another assay described below in Example 6 measures reagent inhibition of primer extension carried out by the Stoffel Fragment of the Taq DNA Polymerase. As is the case with the intact Taq polymerase, inhibition of extension required the presence of modified ends on the oligonucleotide stems and was not significantly affected by the length of the loop between the stem. However, unlike the case of intact Taq polymerase, the Stoffel Fragment is inhibited by compound 6-22DD, a reagent having a stem of only six nucleotides. We conclude that the Stoffel fragment does not interact with the reagent in the same way as does the intact polymerase.

Reagents according to this invention are useful for prevention of mispriming in symmetric PCR assays, as demonstrated below in Example 8. The assay measured amplification of a sequence in the cystic fibrosis gene using an equimolar pair of primers having very similar $T_m$ values.

PCR amplifications and assays currently in use typically include preparation of amplification reaction mixtures at room temperature, thus requiring inclusion of reagents according to this invention in the initial mixture to inhibit Type 1 mispriming. However, that need not be the case. Certain automated methods, for example, microfluidics methods, permit addition of polymerase to a reaction mixture at elevated temperature for a hot start, thereby bypassing Type 1 mispriming. With such methods reagents according to this invention could be added after the start of amplification.

Primer-dimer formation is a manifestation of mispriming that can take place in complete reactions, i.e. those containing all of the components required for amplification plus an initial target sequences, as well as in reactions that do not contain a target sequences. Primer-dimers are typically short double-stranded DNA sequences formed by mispriming of one or more primers in a reaction by hybridization to and extension along either another copy of the same single-stranded primer or some other primer present in the reaction. Primer-dimer formation in the presence of a target sequence is observed as an accumulation of primer-dimers in addition to accumulation of the expected amplicon. Primer-dimer formation in the absence of a target sequence is observed as accumulation of the primer-dimer without accumulation of a specific amplicon. Primer-dimers can also form oligomers that are longer in sequence than the basic primer-dimer because they contain additional, concatenated copies of one or both of the primers. The process of oligomerization is not well understood but is easily detected by gel electrophoresis or melting point analysis of the reaction products. Because of primer-dimer formation the amount of the expected amplicon produced over a given number of thermal cycles is reduced as one or both of the primers is consumed in generation and accumulation of primer-dimers. Elimination of primer-dimers is therefore desirable because it increases both the specificity and yield of the correct product. These features of primer-dimers, as well as their elimination by addition of the reagents described in this invention, are illustrated in Example 10.

The probability of primer-dimer formation is increased by sequence homology between the 3' end of one primer and sequences internal to the same primer or a different primer, in addition to many other factors, for example, elevation of primer concentration, increasing the magnesium concentration, increasing the length of the primer, lowering the annealing temperature of the thermal cycle, and increasing the total number of primers included in reaction. In addition, it is well known in the art that the probably of primer-dimer formation is much higher in reactions employing non-hot-start polymerases as compared to those employing hot-start polymerases. This is because primer-primer hybridization and extension can occur at relatively low temperatures when the components of the reaction are being mixed. Hot-start enzymes reduce, but do not entirely eliminate generation and accumulation of primer-dimers. These features of primer-dimers, as well as their elimination via addition of the reagents described in this invention, are illustrated in Example 11.

Figure 13:
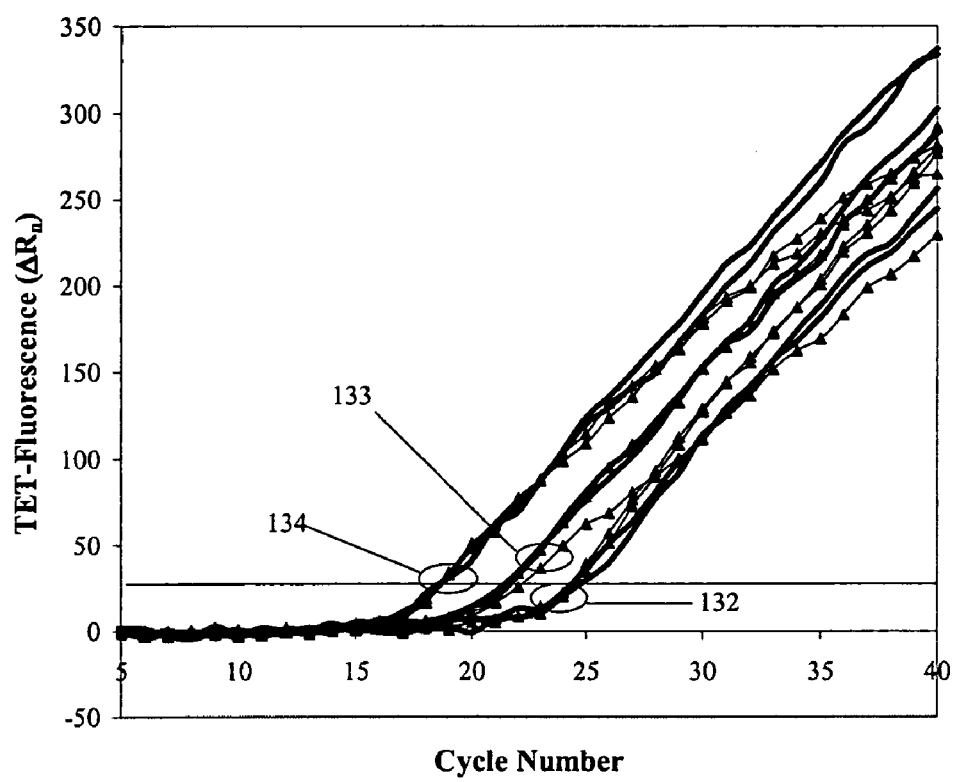
FIG. 13 shows the effect of varying the concentration of reagent 9-3b DD on a duplex LATE-PCR amplification of two target sequences with two primer pairs.
Figure 14:
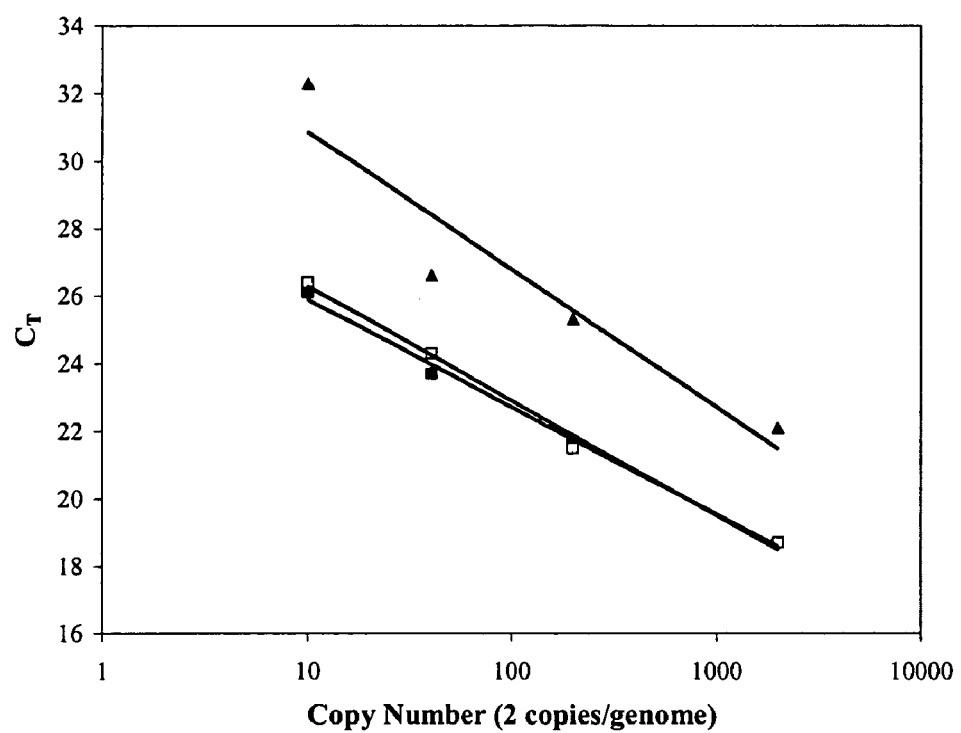
FIG. 14 shows the effect of increasing concentrations of reagent 9-3 DD on the efficiency of a LATE-PCR amplification in terms of $C_T$ values.
Figure 15:
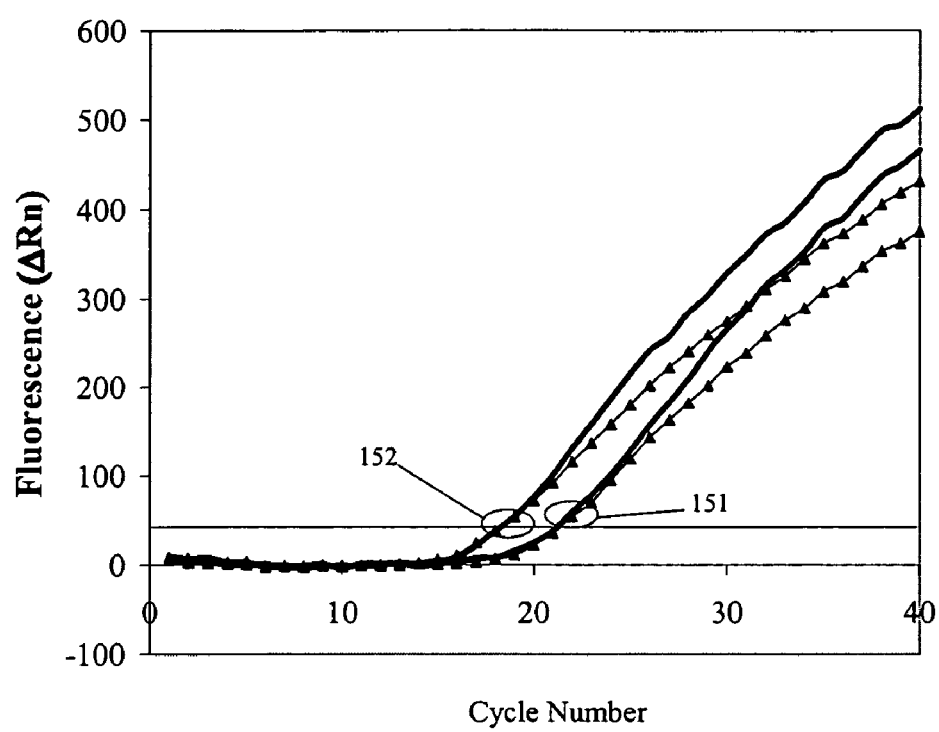
FIG. 15 shows the effect of increasing concentrations of reagent 9-3 DD on the efficiency of a LATE-PCR amplification in terms of fluorescent signal slope and final fluorescence.
Figure 16:
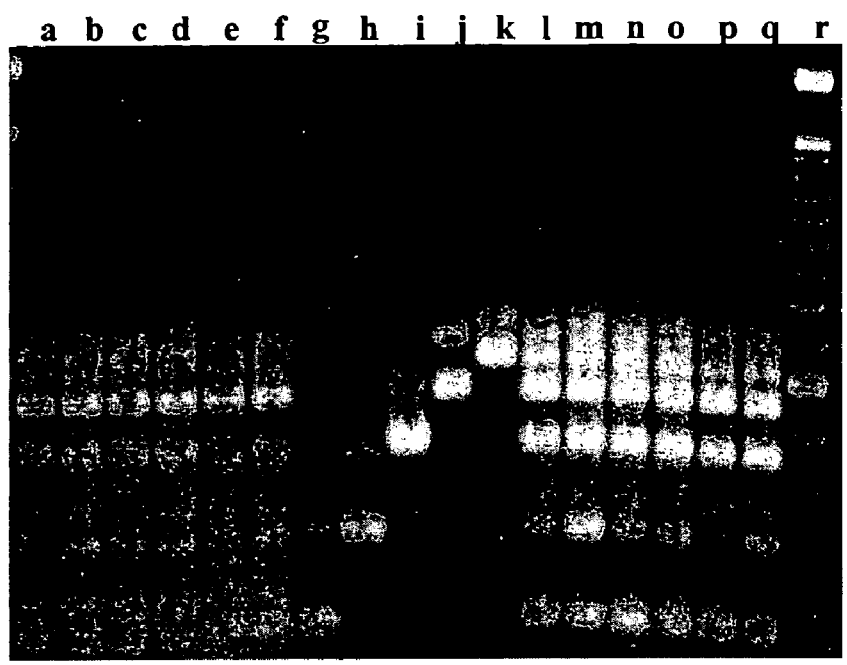
FIG. 16 shows products of a multiplex reaction carried out with and without a mixture of compounds according to this invention.

Formation of primer-dimers can also have subtle effects on the kinetics of a reaction, and their elimination by addition of the reagents described herein can be observed and optimized kinetically. Example 12 describes a LATE-PCR amplification comprised of two pairs of primers and generating two single-stranded products. The kinetic accumulation of one of those products was detected by hybridization to a fluorescent probe, and is shown in FIG. 13 and FIG. 14. The data demonstrate that the linearity of the kinetics is affected by both the precise composition of the stem of the reagent, because of its effect on melting temperature, and by the concentration of the reagent. Moreover, optimal and suboptimal use of reagents can alter the rate of linear amplification in a LATE-PCR and thereby the magnitude of the signal at the end of the reaction without affecting the $C_T$ value of the reaction. FIG. 15 and FIG. 16 demonstrate that amplification efficiency was the same as judged by $C_T$ values over a range of template starting concentrations when compound 9-3DD was used at 150 and 300 nM, but the magnitude of the signals arising from 100 and 1000 template starting numbers in the presence of 300 nM 9-3DD was higher than those obtained using 150 nM 9-3DD, probably because of the absence of primer-dimer formation.

EXAMPLES

Example 1

Rigorous Assay for Assessing Mispriming Errors

In order to assess Type 1, Type 2 and Type 3 mispriming, in PCR amplification reactions, we perform a LATE-PCR amplification utilizing sheared genomic DNA and investigate the products by melting-point analysis and by gel electrophoresis. A particular amplification that we have used is the following:

A. Substrate: 10-10,000 genome equivalents of sheared genomic DNA. The DNA was purchased commercially and processed by freezing and thawing genomic DNA multiple times or by any other similar method known by those skilled in the art for shearing DNA.

B. PCR Amplification Mixture Base (see Sanchez et al. (1994) PNAS 101: 1933-1938):
   Substrate: 2000 genomes of sheared genomic DNA
   1×PCR buffer
   $Mg^{+2}$: at 3 millimolar (mM)
   dNTPs: 250 micromolar (µM) concentration of each of the four dNTP's
   Excess primer: sequence 5'CTTTGATGACGCTTCTG-TATCTA 3'(SEQ ID NO: 13) at 1000 nanomolar (nM)
   Limiting primer: sequence 5'CCTGGATTATGCCTG-GCACCAT 3' (SEQ ID NO: 14) at 50 nM
   DNA polymerase: 1.25 units per 25 microliters (µl) reaction mixture.

C. Amplification Protocol:
   Low-temperature incubation: 35 min. at room temperature.
   PCR Amplification protocol: high-temperature soak at 95° C. for 15 min;
   10 cycles at 95° C. for 10 sec, 55° C. for 30 sec; and 70° C. for 30 sec, followed by 70 cycles of 95° C. for 10 sec, 50° C. for 30 sec, and 70° C. for 30 sec.

A base-line case for mispriming was established by amplifications utilizing two thermostable DNA polymerases, Promega Taq and Invitrogen Taq without use of any hot-start methodology. Additional amplifications were performed utilizing two different commercially hot-start DNA polymerases, Qiagen Hot Star Taq and Platinum Taq (Invitrogen). Finally, additional amplifications were performed with the addition of 300 nM of a currently preferred embodiment of a reagent according to the invention. One embodiment used in this example is a reagent that we refer to as composition 9-22 DD (in our nomenclature "9" is the stem length, "22" is the loop length, and "DD" signifies the stabilizing modification, in this case a pair of Dabcyl quenchers). Compound 9-22 DD has a calculated $T_m$ of 81° C. It has the sequence shown in Table II that is modified by the addition of 5' terminal and 3' terminal Dabcyl moieties.

Gel electrophoresis results of the various amplifications, with ethidium bromide staining, are shown in FIG. 1, which includes size markers (100 base-pair differences) in the unlabeled marginal columns. Duplicates were run, so there are two lanes for the product of each LATE-PCR amplification. Lanes a, a base-line case in which the DNA was omitted; lanes b, a base-line case in which the DNA polymerase was Promega Taq; lanes c, a base-line case in which the DNA polymerase was Invitrogen Taq; lanes d, substitution of the hot-start enzyme Qiagen Hot Star Taq; lanes e, substitution of the hot-start enzyme Platinum Taq; lanes f, amplification utilizing Promega Taq polymerase with the addition of compound 9-22 DD; lanes g, amplification utilizing Invitrogen Taq polymerase and compound 9-22 DD; lanes h, amplification utilizing Qiagen Hot Star Taq DNA polymerase and compound 9-22 DD; lanes i, amplification utilizing Platinum Taq polymerase and compound 9-22DD.

From FIG. 1 it can be seen that regular Taq DNA polymerases that have both polymerization activity and 5'-3' exonuclease activity (lanes b and lanes c) yielded a range of product sizes, almost none of which was the desired amplicon defined by the primer pair, which is the product seen in lanes f-i. Switching to modified "hot-start" polymerases (lanes d-e) helped but still did not eliminate non-specific products formed due to mispriming errors. When compound 9-22 DD was present at 300 nM concentration, however, the desired amplicon was obtained without non-specific products formed due to mispriming errors both when the enzyme was a regular Taq DNA polymerase (lanes f-g) and when the enzyme was a hot-start Taq DNA polymerase (lanes h-i).

Using the rigorous assay of this example, we have compared a number of unmodified and modified DNA hairpin molecules without terminal stabilization; with terminal destabilization as one obtains by adding identical nucleotides to the end of each arm; with terminal stabilization according to this invention; and with non-stabilizing terminal additions. To make the comparison quantitative, we performed dosage response tests using the assay for each compound that exhibited mispriming suppression activity in order to determine the minimum concentration needed to yield elimination of non-specific products formed due to mispriming errors, and the presence of only the desired specific product, obtained as shown in FIG. 1 with regular Taq DNA polymerase. The results are shown in Table I, which includes the calculates stem $T_m$ for each reagent tested. Sequences of the various compounds reported in Table I are set forth in Table II.

TABLE I

| Compound | Modifications | Stem Length/Tm (bp/C) | Loop Length (bp) | Prevent Non-specific Amplification | Lowest concentration (nM) |
|---|---|---|---|---|---|
| 6-22 | None | 6/80 | 22 | No | |
| 9-3 | None | 9/56 | 3 | Yes | 1000 |
| 9-5 | None | 9/93 | 5 | No | |
| 9-22 | None | 9/81 | 22 | Yes | 3000 |
| 11-22 | None | 11/81 | 22 | Yes | 1000 |
| 12-3 | None | 12/56 | 3 | No | |
| 12-C3 | C3 spacer | 12/56 | 3 | No | |
| 12-C3C3 | C3 spacer | 12/56 | 3 | No | |
| 6-22DD | 5'3' dabcyl | 6/80 | 22 | Yes | 3000 |
| 9-3DD | 5'3' dabcyl | 9/56 | 3 | Yes | 100 |
| 9-3bDD | 5'3' dabcyl | 9/62 | 3 | Yes | 100 |
| 9-3iDD | 5'3' dabcyl | 9/68 | 3 | Yes | 100 |
| 9-5DD | 5'3' dabcyl | 9/93 | 5 | Yes | 50 |
| 9-22DD | 5'3' dabcyl | 9/81 | 22 | Yes | 50 |
| 9-5 BHQBHQ | 5'3' Black Hole Quencher™ | 9/93 | 5 | Yes | 100 |
| 9-3 2' OM$^4$ | 2' O'Methyl nucleotides | 9/93 | 3 | Yes | 300 |
| 9-5 2' OM$^4$ | 2' O'Methyl nucleotides | 9/93 | 5 | Yes | 50 |
| 12-3DD | 5'3' dabcyl | 12/58 | 3 | Yes | 50 |
| 12-3bDD | 5'3' dabcyl | 12/63 | 3 | Yes | 100 |
| 12-3cDD | 5'3' dabcyl | 12/68 | 3 | Yes | 100 |
| 12-C3DD | C3 spacer 5'3' dabcyl | 12/56 | 3 | Yes | 300 |
| 12-C3C3DD | C3 spacer 5'3' dabcyl | 12/56 | 3 | Yes | 300 |
| 9-22-3D | 3' dabcyl | 9/81 | 22 | Yes | 1000 |
| 9-22-5D | 5' dabcyl | 9/81 | 22 | No | |
| 9-22FF | 5'3' Fam | 9/81 | 22 | No | |
| 9-22AA | 5'3' AA | 9/85 | 22 | No | |
| 9-22TT | 5'3' TT | 9/78 | 22 | No | |
| 9-22TT 5D | 5'3' TT with 5' dabcyl | 9/78 | 22 | No | |

TABLE II

| Compound | Sequence | SEQ. ID NO. |
|---|---|---|
| 6-22 | GGCGTCAGGCATATAGGATACCGGGACAGACGCC | 1 |
| 9-3 | CATTATAATGAAATTATAATG | 2 |
| 9-5 | CGCGGCGTCATATAGACGCCGCG | 3 |
| 9-22 | CGCGGCGTCAGGCATATAGGATACCGGGACAGACGCCGCG | 4 |
| 11-22 | GCTCGCTGCCGACCGTATATCCTATGGCCCTGACGGCAGCGAGC | 5 |
| 12-3 | CTTAATTATAATGAAATTATAATTAAG | 6 |
| 12-C3 | CTTAATTATAAT-(CH$_2$)$_3$-ATTATAATTAAG | 7 |
| 12-C3C3 | CTTAATTATAAT-(CH$_2$)$_3$(CH$_2$)$_3$-ATTATAATTAAG | 8 |
| 9-3b | CGTTATAATGAAATTATAACG | 9 |
| 9-3i | CGCTATAATGAAATTATAGCG | 10 |
| 12-3bDD | CGTAATTATAATGAAATTATAATTACG | 11 |
| 12-3cDD | CGCTATTATAATGAAATTATAATAGCG | 12 |

Table I compares several DNA hairpins, with and without modifications and identifies several terminally stabilized hairpin molecules that are reagents according to this invention (clean amplicon without products of mispriming at less than 1000 nM concentration) or that are preferred reagents according to this invention (clean amplicon without products of mispriming at no more than 650 nM concentration). The unmodified hairpins are identified by two numbers, the first being the stem length and the second being the loop length. Compounds according to this invention appearing in Table I have several stabilizing modifications: a 5' Dabcyl quencher and a 3' Dabcyl quencher covalently attached to the terminal nucleotides by means of a commercial linker (signified by the suffix "DD"), a 3' Black Hole™ quencher and a 5' Black Hole™ quencher similarly attached (signified by the suffix "BHQBHQ"), and two 3' 2'-O-methyl ribonucleotides and two 5' 2'-O-methyl ribonucleotides substituted for deoxyribonucleotides at the stem terminus (signified by "2'OM$^4$"). Destabilizing modifications to the stem termini included substituting a pair of A's or T's at the 3' and 5' ends of the molecule. Adding a pair of FAM fluorophores, which are not believed to interact with one another in a stem-stabilizing fashion, was destabilizing, as was adding a single 5' Dabcyl. However, adding a single 3' Dabcyl slightly stabilized the 9-22 hairpin, as shown by a drop in the concentration required. Hairpin 9-22, suppressed mispriming only at high (3000 nM) concentration, but 9-22 DD did so at low concentration (50 nM).

Another of our presently preferred hairpins, compound 9-3, suppressed mispriming only at high (1000 nM) concentration, but 9-3 DD and 9-3 2'OM$^4$ did so at much lower concentration (100-300 nM). Yet another embodiment, 9-5 DD, 9-5 BHQBHQ and 9-5 2'OM$^4$ did so also at low concentrations (50-100 nM). Oligonucleotide 9-5 has the same stem as oligonucleotide 9-22 but a shorter loop whose nucleotides are A's and T's. The calculated stem T$_m$ of oligonucleotide 9-5 is 93° C., some 12° C. higher than the calculated stem T$_m$ of oligonucleotide 9-22 due to the influence of the loops.

Similar results were obtained with an even longer stem. Compound 12-3 did not suppress mispriming, but compound 12-3DD was effective at only 50 nM concentration.

Table I shows that stabilized stems can be modified to change the calculated stem melting temperature (Tm). For example, compound 9-3DD, Tm 56° C., was effective at 100 nM concentration. By altering the G-C content of the stem we created compounds 9-3bDD (Tm 62° C.) and 9-31DD (Tm 68° C.). Both were also effective at 100 nM concentration. Compound 12-3DD, Tm 58° C., was effective at 50 nM concentration. Compounds with altered stems, namely, compound 12-3bDD, Tm 63° C., and compound 12-3cDD, Tm 68° C., were effective at a 100 nM concentration, still very good.

Example 2

LATE-PCR End-Point Assay

Figure 2:
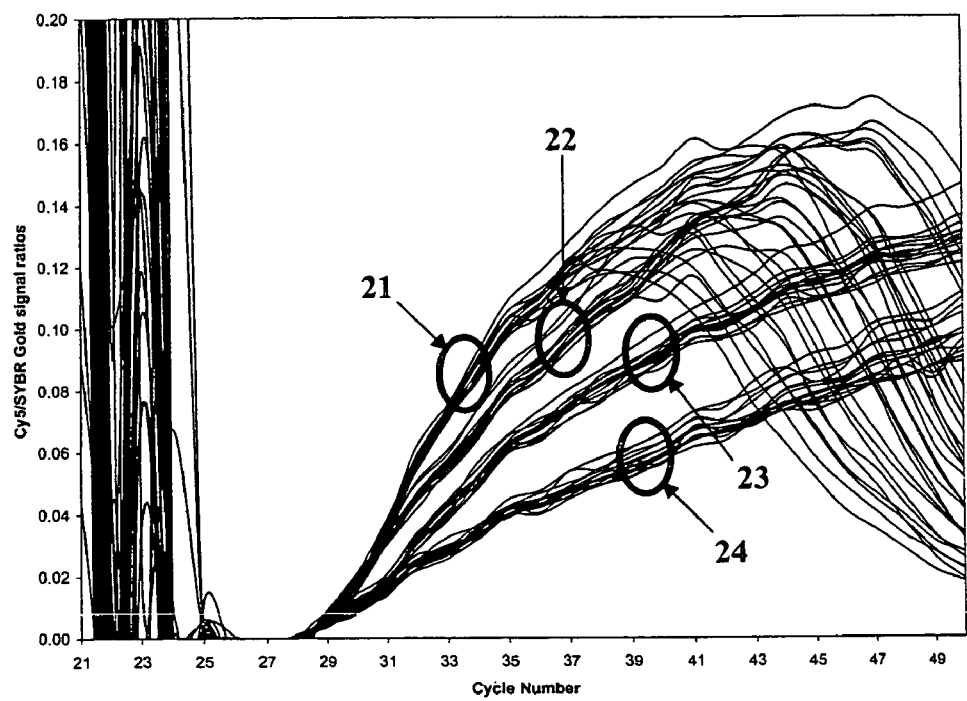
FIG. 2 shows that reagents according to this invention enable PCR-based real-time and end-point assays.

Stochastic variation in reaction kinetics among replicate samples results in scatter of signals from hybridization probes and hampers end-point analysis. LATE-PCR significantly reduces that problem. Utilization of a reagent according to this invention further improves the ability to utilize end-point detection. FIG. 2 presents results obtained in amplifying an amplicon that includes the G269 allele of the hexosaminidase A gene responsible for Tay Sachs disease. The reaction mixture contained 0.6 µM hybridization probe and either 1000 genomes homozygous wild type DNA target (+/+) or heterozygous DNA target (G269/+). Replicate samples of each type were amplified as follows: 1×PCR buffer, 3 mM $MgCl_2$, 250 µM of each dNTP, 25 nM Limiting Primer having a sequence 5'CGAGGTCATTGAATACGCACGGCTCC 3' (SEQ ID NO: 15), 1000 nM Excess Primer having a sequence 5' TAACAAGCAGAGTCCCTCTGGT 3' (SEQ ID NO: 16), 1.25 units Platinum (hot-start) Taq polymerase, 0.6 µM Cy5-labeled hybridization probe having a sequence 5'Cy5-GG-GACCAGGTAAGAA-phosphate 3' (SEQ ID NO: 17), and a 1:40,000 dilution SYBR Gold I in the presence or absence of 100 nM of embodiment 9-22 DD in 25 µl reactions. PCR cycle parameters were 95° C. for 3 minutes; 25 cycles at 95° C. for 10 sec, 65° C. for 20 sec, and 72° C. for 20 sec; and 30 cycles at 95° C. for 10 sec, 65° C. for 20 sec, 72° C. for 20 sec, 55° C. for 20 second, and 45° C. for 20 sec with fluorescence acquisition at 72° C. for SYBR Gold, and fluorescence acquisition at 55° C. and 45° C. for Cy5. To correct for tube-to-tube variations in reaction kinetics, hybridization signals were normalized by the ratio of Cy5 signals at 55° C. to SYBR Gold signals at 72° C. One consequence of such normalization is that any $C_T$ delay is masked.

FIG. 2, lines identified by circle 21 and lines identified by circle 22, show the results of multiple replicates without addition of a reagent according to this invention but with hot-start polymerase. Homozygous replicates (circle 21) and heterozygous replicates (circle 22) can be distinguished by the slopes of their linear plots. Scatter among replicates and mispriming errors in these samples, evidenced by the drop in hybridization probe signal (the "hook effect") after about 40 cycles precludes end-point identification of these samples. FIG. 2, lines identified by circles 23-24, show the results with addition of reagent according to this invention, namely, 100 nM 9-22 DD. Under these conditions mispriming errors do not occur, linear kinetics are preserved in the course of the assay, scatter is reduced, the hook effect is avoided, and end-point identification of homozygous and heterozygous samples is possible at 50 cycles.

Example 3

Preparing DNA Samples for Dideoxy Sequencing

LATE-PCR is a non-symmetric amplification method that potentially generates large amounts of single-stranded DNA suitable for DNA sequencing when the amplification reaction is carried out over 60 and more thermal cycles. However, such large numbers of amplification cycles encourage the appearance of products of mispriming, believed to include the formation of Type 2 and Type 3 mispriming errors, that manifest themselves by accumulation of detectable non-specific products that eventually become the predominant species in the reaction. Reagents according to this invention allow the synthesis of large amounts of single-stranded DNA suitable for DNA sequencing in the absence of non-specific products when using 70 and more cycles of LATE-PCR amplification. Samples suitable for dideoxy sequencing by capillary gel electrophoresis were prepared as follows. LATE-PCR reaction mixture was first prepared in 25 µl containing 1×PCR buffer, 3 mM $MgCl_2$, 1000 nM Excess Primer having the sequence 5' GCCAGGGGTTCCACTACGTAGA 3' (SEQ ID NO: 18, 25 nM Limiting Primer having the sequence 5'CCGCCCTTCTCTCTGCCCCCTGGT 3' (SEQ ID NO: 19), 1.25 units Platinum Taq polymerase, 600 nM reagent 9-3 DD and 250 µM of each dNTP. Compound 9-3 DD has a Dabcyl quencher added to each terminal nucleotide of oligonucleotide 9-3. Amplification was carried out at 95° C. for 3 minutes; 10 cycles at 95° C. for 10 sec, 65° C. for 20 sec, and 72° C. for 20 sec; and 60 cycles at 95° C. for 10 sec, 65° C. for 20 sec, 72° C. for 20 sec; and 45° C. for 20 sec. Parallel reactions were performed with either 1:40,000 dilution SYBR Green or 2.4 µM Low $T_m$ molecular beacon having the sequence 5'FAM-CGTGCGCTCTGGTAAGGGTTTG-CACG-Dabcyl 3' (SEQ ID NO: 20) to monitor double-stranded and single-stranded DNA synthesis separately. Each sample contained 6 ng (about 1000 genomes) of human DNA. Further, a control was run without addition of compound 9-3 DD.

Results of the amplification reactions were that the control with hot-start Taq DNA polymerase but not compound 9-3 DD manifested significant mispriming, as evidenced by a secondary rise in SYBR Green signal during the late stages of amplification, after the Limiting Primer had been depleted. Because the product was such a mixture, it was not possible to sequence the control. On the other hand, results of the amplification with compound 9-3 DD added showed the presence of only the desired specific product without a delayed rise in the SYBR Green signal through 70 cycles. We calculated, from the Limiting Primer concentration and an assumed efficiency of linear amplification of 50%, that the reaction generated 250 fmoles/µl of clean product. That product was submitted to the Brandeis University dideoxy sequencing facility for sequencing.

Figure 3:
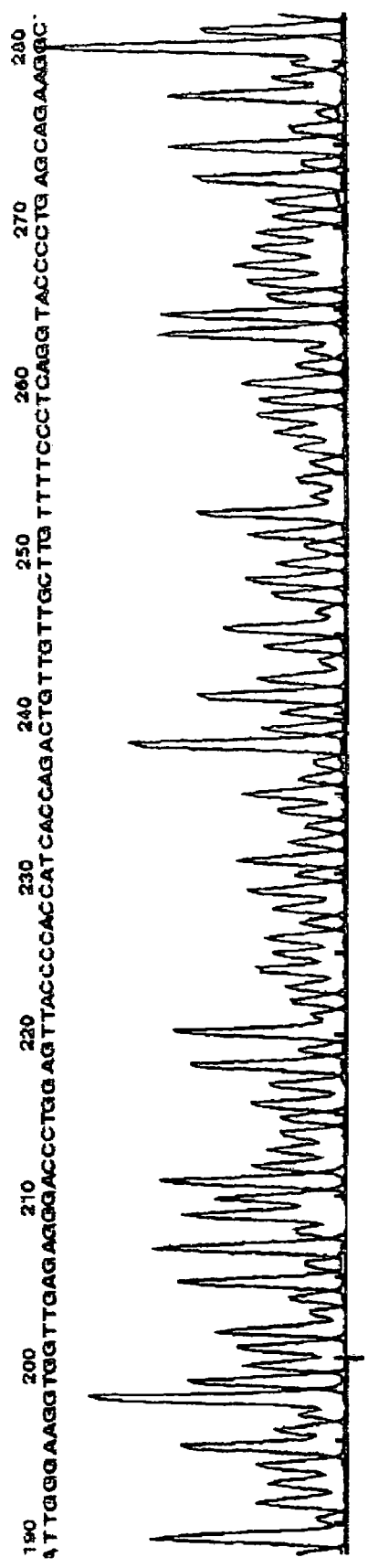
FIG. 3 shows a DNA sequence chromatograph obtained from single-stranded DNA products (SEQ ID NO:50) generated after 70 cycles of LATE-PCR amplification in the absence of mispriming errors using the reagents described in this invention.

The sequencing reaction was performed using a standard protocol, as was capillary electrophoresis utilizing a Beckman CEQ 2000 DNA Sequencer. The sequencing reaction was performed with a ⅕ aliquot of the amplified product, that is, with only 50 fmoles of product. The machine-produced sequence is presented in FIG. 3, which shows the sequence along the upper portion of the chart, the clear, unambiguous product peaks from which the sequence was derived, and, at the bottom a very low level of background signal. We confirmed the correctness of the machine-produced sequence by comparing it to the known sequence of the amplicon available from GenBank Accession No. NT 010235.

Example 4

Multiplexed PCR Amplification

Suppression of mispriming errors is particularly critical in multiplexed reactions where multiple products are amplified simultaneously. The presence of several primer pairs and amplification products increases the probability of mispriming interactions between and among these reactive species. Multiplexed reactions composed of increasing numbers of amplicons were carried out in the absence or presence of compound 9-3 DD. LATE-PCR reactions, 25 µl volume, consisting of sample, 1×PCR buffer, 3 mM MgCl$_2$, 100 µM of each dNTP, 1000 nM Excess Primer, 50 nM Limiting Primer, and 1.25 units of non-hot-start Promega Taq polymerase were set up in the absence or presence of 300 nM reagent 9-3 DD for different combinations of primer pairs as indicated below. Samples were amplified using a thermal cycling profile of 95° C. for 3 minutes; 10 cycles at 95° C. for 10 sec, 65° C. for 30 sec, and 70° C. for 30 sec; and 40 cycles at 95° C. for 10 sec, 50° C. for 30 sec, 70° C. for 30 sec. At the end of the reaction the samples were analyzed by gel electrophoresis in a 3.5% agarose gel in 0.5×TBE. The intended amplicons and primers pairs tested were as following Reaction A: two regions TSD 1278+TSD 1421 of the Hex-A gene associated with Tay Sachs disease.

```
TSD 1278 Excess Primer:
5' GCCAGGGGTTCCACTACGTAGA 3'     (SEQ ID NO:21)

TSD 1278 Limiting Primer:
5' CCGCCCTTCTCTCTGCCCCCTGGT 3'   (SEQ ID NO:22)

TSD 1421 Excess Primer:
5' CCGGGTCTCTAAGGGAGAACTCCT 3'   (SEQ ID NO:23)

TSD 1421 Limiting Primer:
5' CCGGCCGACAACACAAACCTGGTCC 3'  (SEQ ID NO:24)
```

Reaction B: TSD 1278 amplicon, TSD 1421 amplicon, and a region of the CFTR gene, the CF exon 10 amplicon.

This reaction contained the same as primer pairs at Reaction A plus

CF ex10 Excess Primer: 5' GCTTTGATGACGCTTCTGTATCTA 3' (SEQ ID NO: 25)

CF ex 10 Limiting Primer: 5'CAGTTTTCCTGGATTATGCCTGGCACCAT 3' (SEQ ID NO: 26)

Reaction C: TSD 1278 amplicon, TSD 1421 amplicon, CF exon 10 amplicon, and another region of the CFTR gene, the CF exon 11 amplicon.

This reaction contained the same as primer pairs at Reaction B plus

CF ex 11 Excess Primer: 5' TCGAAGTTTGCAGAGAAAGACAAT 3' (SEQ ID NO: 27)

CF ex 11 Limiting Primer: 5' TGACGTTTACAGCGAATGCTTGCTAGACCAAT 3' (SEQ ID NO: 28)

Reaction D: TSD 1278 amplicon, TSD 1421 amplicon, CF exon 10 amplicon, CF ex11 amplicon, and a region of the human beta globin gene.

This reaction contained the same as primer pairs at Reaction C plus

Beta Globin Excess Primer: 5' TGGGTTTCTGATACGCACTGACTCTCTC 3' (SEQ ID NO: 29)

Beta Globin Limiting Primer: 5' GGCCATCACTAAAGGCACCGAGCACT 3' (SEQ ID NO: 30)

Figure 4:
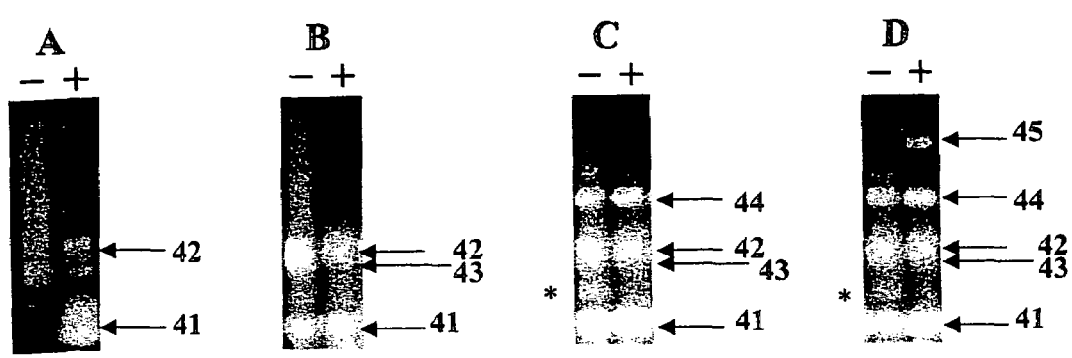
FIG. 4 shows the effect of compound 9-3 DD on a pentaplex LATE-PCR amplification.

Electrophoresis gels were stained with ethidium bromide to detect double-stranded products produced during the exponential phase of the LATE-PCR reaction. FIG. 4 shows pertinent portions of gels of products from multiplexed reactions A through D. Arrows point to specific double-stranded amplification products, unnumbered bands correspond to specific single-stranded DNA products with secondary structure, and asterisks identify non-specific products. Gel pairs A-D correspond to reactions A-D, respectively. Each gel labeled "+" is product from amplification including compound 9-3 DD. Each gel labeled "−" is product from amplification without compound 9-3 DD.

Gel pair A shows that, in the absence of 9-3 DD compound region TSD 1278 (arrow 41) did not amplify but region TSD 1421 (arrow 42) did amplify, along with a large number of non-specific products, predominantly or entirely double-stranded, that appeared in the gel as a smear. Addition of the 9-3 DD compound reduced the background of non-specific products and allowed amplification of both TSD 1278 (arrow 41) and TSD 1421 (arrow 42) amplified more cleanly, showing that several manifestations of mispriming were prevented.

Gel pair B shows that in the absence of 9-3 DD compound regions TSD 1278, TSD 1421, and CF exon 10 (arrow 43) amplified along with a large number of non-specific products that appeared in the gel as a smear. Addition of the 9-3 DD compound eliminated the background non-specific products, and all three expected amplicons were obtained.

Gel pair C shows that in the absence of 9-3DD compound regions TSD 1278, TSD 1421, CF exon 10, and CF exon 11 (arrow 44) amplified along with a non-specific product indicated by the asterisk. Addition of the 9-3 DD compound eliminated synthesis of the non-specific product, and all four expected amplicons were obtained.

Gel pair D shows that, in the absence of 9-3 DD compound the selected region of the beta globin gene (arrow 45) did not amplify but TSD 1278, TSD 1421, CF exon 10, and CF exon 11 did amplify, along with a non-specific product indicated by the asterisk. Addition of the 9-3 DD compound eliminated synthesis of the non-specific product and allowed amplification of all five expected amplicons.

We have also demonstrated the use of a compound according to this invention in multiplex amplification and detection reactions when only one target is present in any given test sample, such as may occur when screening for an infecting pathogen. In such a case multiple pairs of primers (we utilized multiple pairs of Excess Primers and Limiting Primers for LATE-PCR amplifications) are present, but only one primer pair will be active for a particular sample. As indicated by SYBR green fluorescence and post-amplification electrophoretic analysis, that is in fact what occurred, demonstrating that compounds of this invention effectively inhibit mispriming in multiplex reactions when fewer than all substrates are present.

Example 5

Relation Between Stem T$_m$ and Annealing Temperature

Two different LATE-PCR amplification protocols were compared utilizing the same amplification mixture, including target. Each amplification was performed both with 600 nM compound 9-3 DD and without compound 9-3 DD. As indicated earlier the stem T$_m$ of compound 9-3 DD (that is, the calculated melting temperature of unmodified oligonucleotide 9-3) is 56° C. Hot-start Platinum Taq DNA polymerase was used. The two amplifications differed primarily in the primer annealing temperature that was employed, either 65° C. (above the stem T$_m$) or 55° C. (below the stem T$_m$). The amplification cycle parameters were:

Profile A: 95° C. for 3 minutes; ten cycles of 95° C. for 10 sec, 65° C. for 20 sec, 7° C. for 20 sec; sixty cycles of 95° C. for 15 sec, 55° C. for 20 sec, 72° C. for 20 sec, 50° C. for 20 sec.

Profile B: same as profile A, except that the last sixty cycles were 95° C. for 10 sec, 65° C. for 20 sec, 72° C. for 20 sec, 45° C. for 20 sec.

The amplification reactions were monitored in real time using SYBR Green I fluorescent dye to monitor the synthesis of double-stranded product, which plateaus in a LATE-PCR reaction following exhaustion of Limiting Primer, unless mispriming causes a variation in the later portion of an amplification. Readings were taken during the low-temperature detection step.

Figure 5:
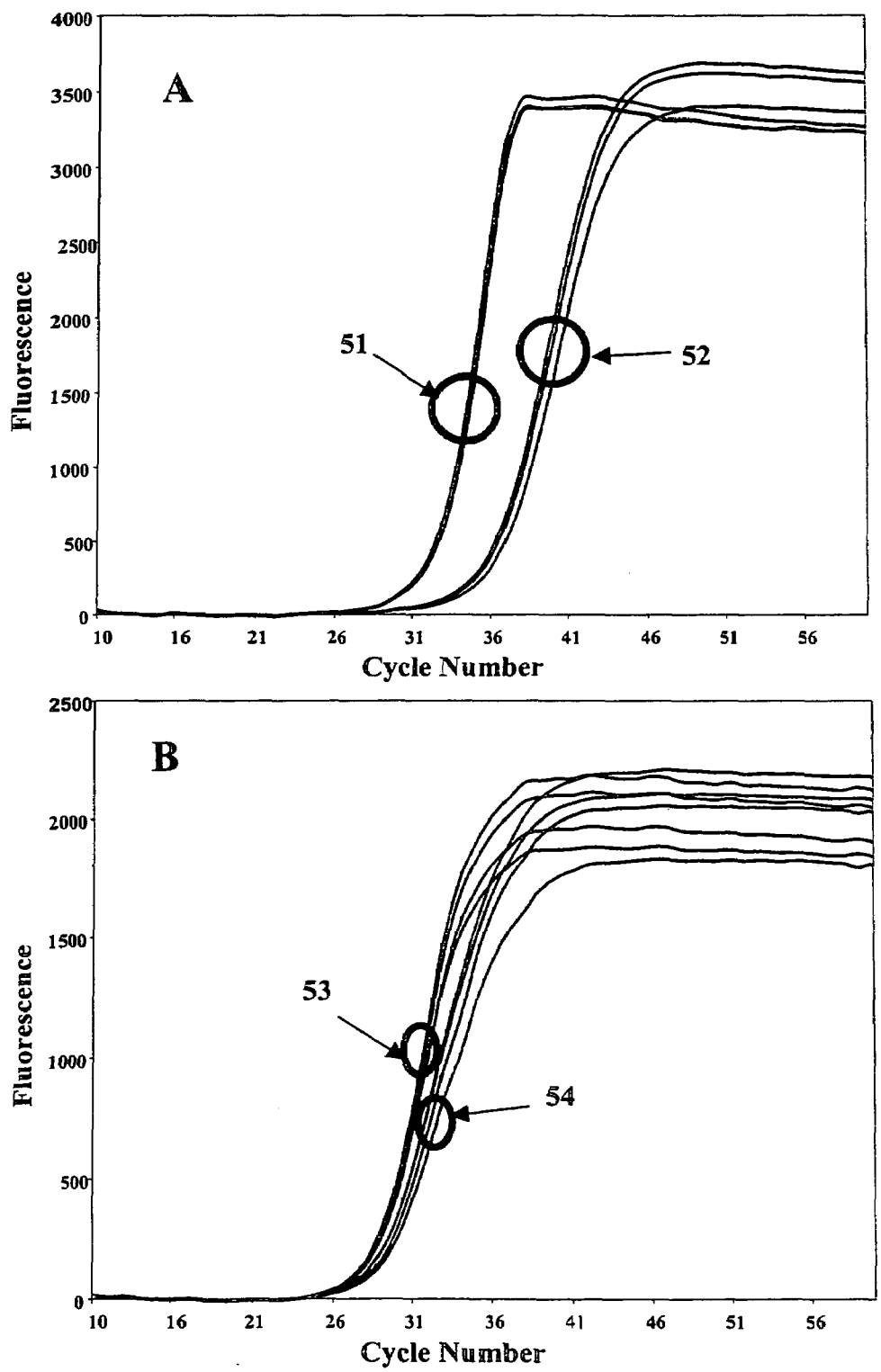
FIG. 5 shows evidence that once the reagents according to the invention bind Taq polymerase they are not released from the polymerase until PCR cycling temperatures reach the denaturation step.

Results are presented in FIG. 5. Panel A shows the fluorescence readings from replicate samples of Profile A, when the 55° C. annealing temperature was utilized after ten cycles of extension, both with (circle 52) and without (circle 51) inclusion of compound 9-3 DD. Panel B shows the fluorescence readings from replicate samples of Profile B, when the 65° C. annealing temperature was used after ten cycles of extension, both with (circle 54) and without (circle 53) inclusion of compound 9-3 DD.

FIG. 5 shows that when a primer annealing temperature below the stem $T_m$ of the reagent of this invention was used (Panel A), a delay of several cycles in the threshold cycle, $C_T$, was observed. However, when the primer annealing temperature was maintained significantly above the stem $T_m$ throughout the exponential PCR phase (Panel B), little, if any, $C_T$ delay was observed. It was noted that for the particular amplicon utilized in this amplification, no Type 2/Type 3 mispriming was observed with or without compound 9-3 DD when hot-start Taq was used, showing the unpredictability of the occurrence of such mispriming errors. This example demonstrates that the stem of reagent 9-3 DD is closed when the temperature of the reaction drops to 55° C. and that the reagent remains bound to the polymerase during the higher-temperature extension step of the reaction.

Example 6

Effect on DNA polymerase activity at 25° C.

A series of primer extension experiments was run at 25° C. to evaluate the effect of reagents according to this invention and their unmodified oligonucleotide analogs. Each reaction mixture included a template, a primer and Taq DNA polymerase. The reaction was carried out for two hours in each case. The primer was fluorescently labeled with Cy5. SYBR Green fluorescent dye was added to the reaction mixture. Following the extension reactions, melt curves were run, in which the dye was stimulated and fluorophore emission due to FRET transfer from the dye was read, as disclosed in our concurrently filed United States Provisional patent application titled Primers, Probes and Methods for Nucleic Acid amplification. Results are presented in FIG. 6.

Figure 6:
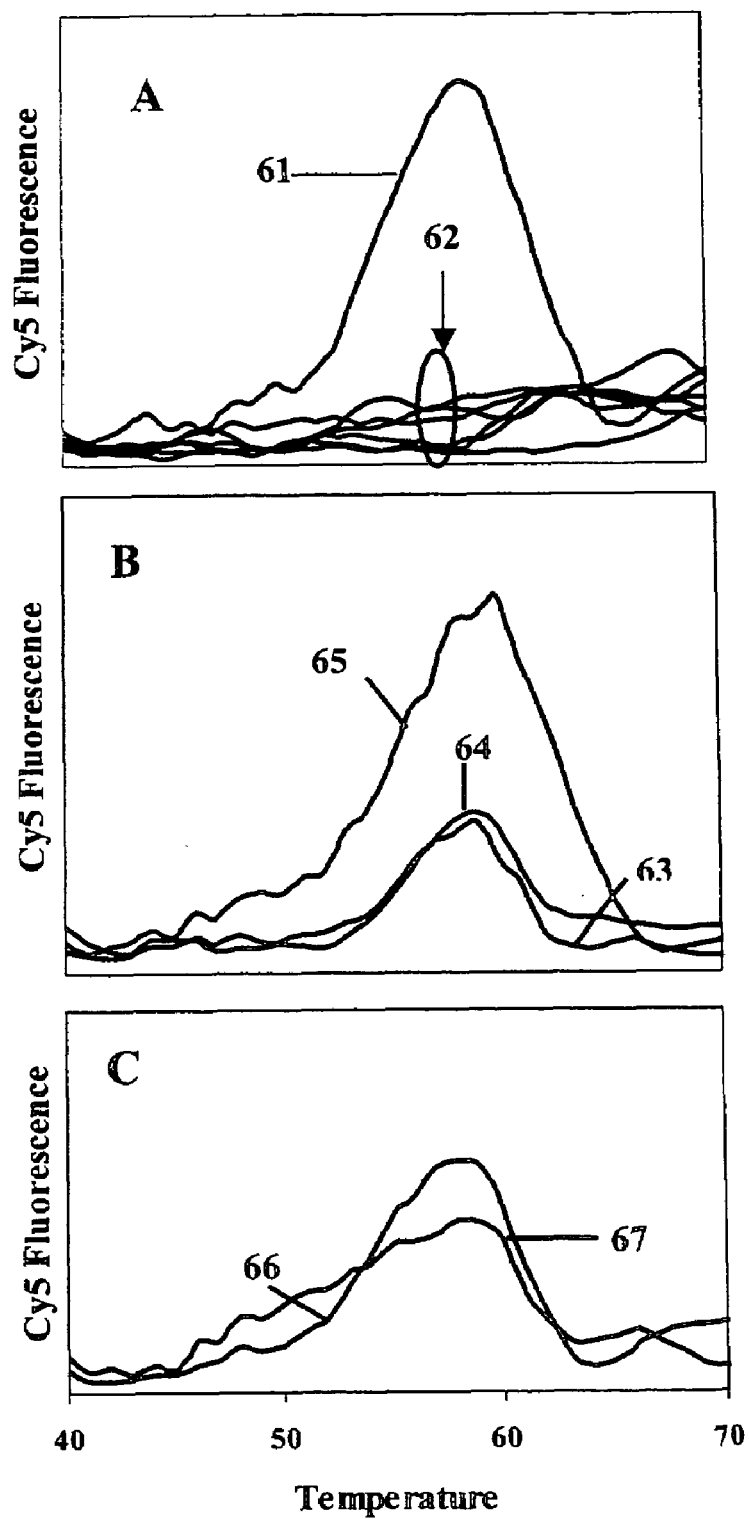
FIG. 6 shows a direct comparison of reagents according to this invention for their effect on DNA polymerase activity at 25° C.

FIG. 6, panel A, includes melting curve 61, obtained when extension was precluded by omitting dNTPs from the reaction mixture. Curve 61 is thus the melting curve of the primer-target hybrid, showing a $T_m$ of 58° C. Panel A also includes several controls which contained dNTPs, either alone or with unmodified oligonucleotide 9-3 (300 nM, 1000 nM) or 9-22 (50 nM, 100 nM, 300 nM). Curves identified by circle 62 for the controls show extension in all cases, that is, the primer melting peak at 58° C. disappeared. FIG. 6, panel B shows a dose-dependent effect of including reagent 9-22 DD in the reaction mixture: curve 63, 50 nM; curve 64, 100 nM; curve 65, 300 nM. The larger the peak at 58° C., the greater the effect of preventing extension by polymerization under the isothermal test conditions. FIG. 6, panel C shows a dose-dependent effect of including reagent 9-3 DD in the reaction mixture: curve 66, 300 nM; curve 67, 1000 nM. Again, the larger the peak at 58° C., the greater the effect of preventing extension by polymerization under the test conditions.

We also investigated the effect on the Stoffel Fragment (Lawyer et al. (1993) PCR Methods and Applications 2: 275-287), a DNA polymerase lacking 5'-3' exonuclease activity. We compared various compounds listed on Table 1 with a negative control containing only template, fluorescently labeled primer, the Stoffel Fragment and dNTPs. In this series, extension was performed at 40° C. and SYBR Green readings were taken every 20 seconds for more than 30 minutes. Curves were compared by eye, that was reliable, because either the curve obtained tracked the control almost precisely or else the curve obtained differed markedly from the control. Test compounds were added at 50 nM, 100 nM and 300 nM concentration. Unmodified hairpins 6-22, 9-3,9-5 and 9-22 did not suppress elongation by the Stoffel Fragment at any concentration. Compound 6-22DD suppressed elongation at all three concentrations, as did compounds 9-3DD, 9-5DD and 9-22DD. The following compounds did not suppress elongation at 50M or 100 nM concentration but did suppress elongation at 300 nM concentration: 9-22-5D, 9-22-3D, 9-5 2'0M$^4$, 9-5BHBHQ, and 9-32'0M$^4$.

Example 7

Effect on Taq Exonuclease Activity in the Absence of Polymerase Activity

We have discovered an assay that demonstrates inhibition of 5'- to -3' exonuclease activity in the absence of DNA synthesis. The assay uses as a substrate a specific double-stranded DNA molecule where one strand is labeled with a FAM fluorophore at the 5' end and the other strand is labeled at the 3' end with a Dabcyl quencher. The fluorophore is in close proximity with the quencher, and fluorescence does not occur when the fluorophore is stimulated. Strand denaturation and annealing upon heating and cooling causes cleavage of the FAM-labeled strand and fluorophore release. We believe that cycling somehow generates a substrate for the 5'- to -3' exonuclease activity of Taq polymerase. Fluorescence increase therefore provides a measure of Taq polymerase 5'- to -3' exonuclease activity.

The 25 µl reaction mixture contains 300 nM double-stranded DNA template in 1×PCR buffer, 3 mM MgCl$_2$, 1.25 units, (U), Taq polymerase, and the presence or absence of an appropriate concentration of 9-22 DD compound. The reactions do not contain any dNTP nor any other nucleic acid target besides the double-stranded DNA. The sequences of the complementary strands of the double-stranded DNA template are 5'FAM-AGTGTGATGATGGTGAGG-phosphate 3' (SEQ ID NO: 31) and 5'-ACTTTCAACTCTGTCT 3'-Dabcyl (SEQ ID NO: 32). Samples are denatured at 95° C. for 3 minutes and then subjected to cycles of 95° C. for 10 sec, 67° C. for 30 sec, 72° C. for 30 sec, and 45° C. for 20 sec. Fluorescence is acquired during each cycle at 45° C.

Fluorescence readings from performance of the assay on several samples are reported in FIG. 7, in which readings are normalized to begin at the same background fluorescence. Curve 76 is a control showing the fluorescence with no Taq polymerase present. Taq polymerase was included in the remaining samples. Curve 71 shows the fluorescence increase resulting when reagent 9-22 DD was not added. Fluorescence rose steadily over thirty cycles. Curves 72-75 show the fluorescence increase with reagent 9-22 DD included at concentrations of 50 nM, 100 nM, 200 nM and 300 nM, respectively. Addition of the 9-22 DD compound to the above reaction reduced the observed fluorescence increase in a dose-dependent manner.

Example 8

Symmetric PCR Amplification

We performed a real-time PCR amplification assay utilizing sheared genomic DNA and a pair of primers of similar $T_m$ in equimolar concentration. We performed replicate assays without and with addition of 400 nM reagent 9-3 DD. The effects of the reagent were evaluated in terms of the kinetics of total DNA accumulation via staining with SYBR Green, as well as by gel electrophoresis with ethidium bromide staining.

The intended target for amplification was an allele of the CFTR gene that occurs in intron 19 as a single base transition (GenBank Accession No. AC000061). The 25 µl reaction mixture contained a substrate of 120 picograms, (pg), of sheared human genomic DNA, 1×PCR buffer, 5 mM $MgCl_2$, 250 µM of each dNTP, a 1:40,000 dilution of SYBR Green, 1000 nM forward primer: sequence 5' TAATTACAA-GAGTCTTCCAT 3' (SEQ ID NO: 33), Tm 56.6° C., and 1000 nM reverse primer: sequence 5' CATGAATAGAA-CATTTCCTT 3' (SEQ ID NO: 34), $T_m$ 56.3° C., and 1.25 units of non-hot-start Invitrogen Taq polymerase in the absence or presence of 400 nM of reagent 9-3 DD. Samples were amplified using a thermal cycling profile of 95° C. for 3 minutes; 60 cycles at 95° C. for 10 sec, 55° C. for 30 sec, and 72° C. for 30 sec with SYBR Green I fluorescence monitored at 72° C., and finally a temperature gradient of 54° C. to 96° C. at 1° C. increments for 30 sec. At the end of the reaction several randomly selected samples from each set of reactions were analyzed by gel electrophoresis in a 3.0% agarose gel in 0.5×Tris, Boric Acid, EDTA Solution (TBE).

Figure 8:
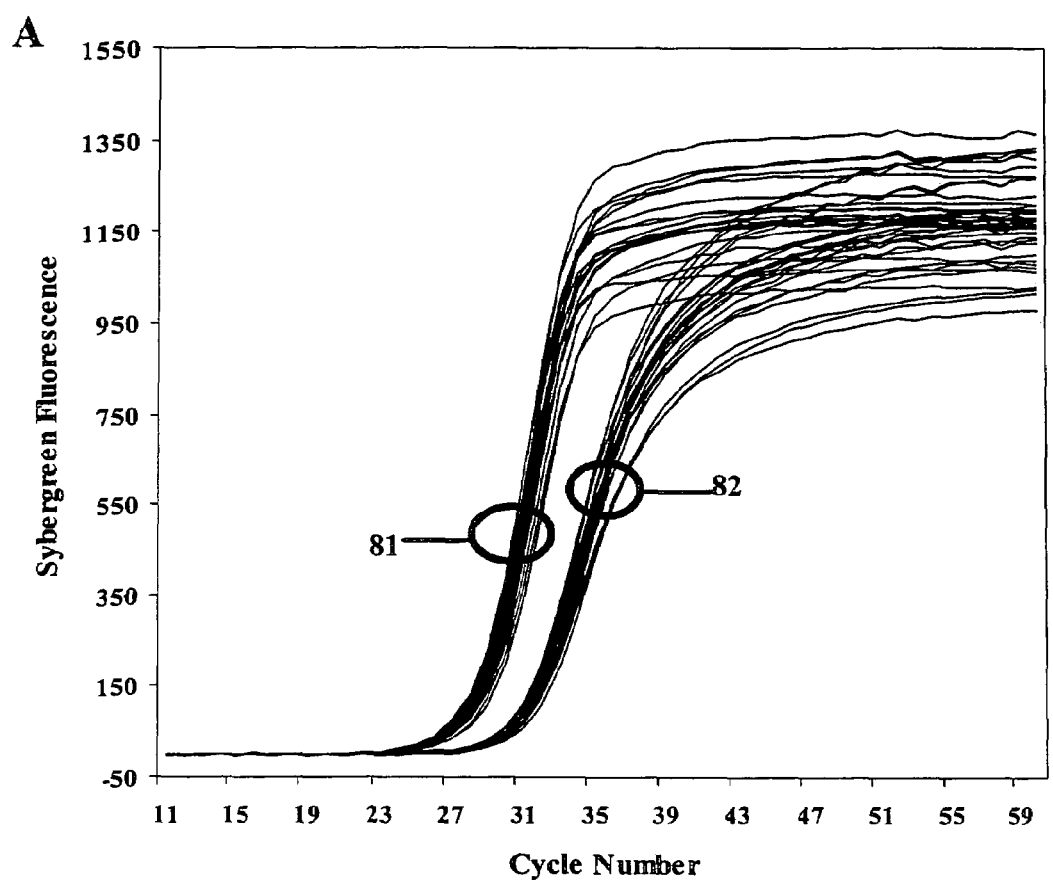
FIG. 8 illustrates the capacity of a reagent according to this invention to prevent mispriming in a symmetric PCR assay.
Figure 8:
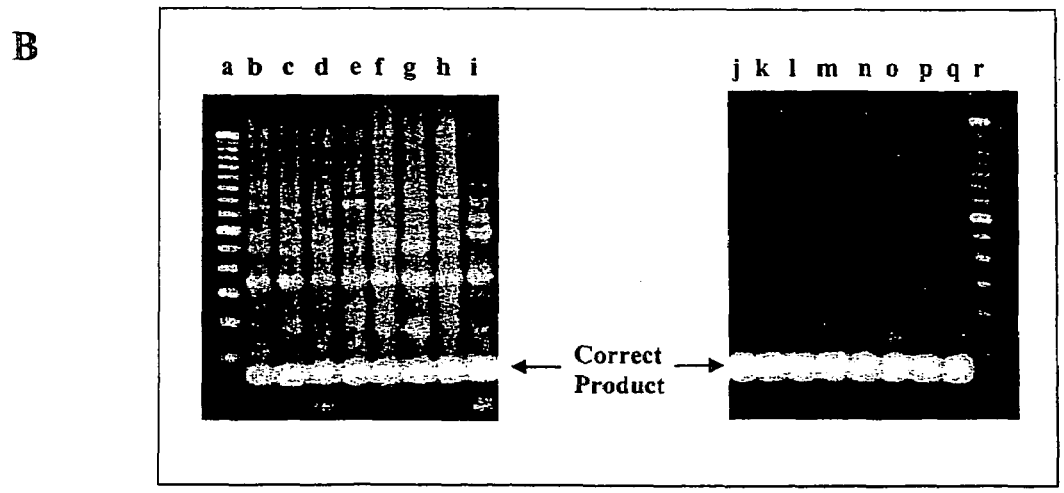

FIG. 8 presents the results obtained. The amplification plot in panel A of FIG. 8 shows the SYBR Green I fluorescence for 60 cycles with curves identified by circle 81 being the replicate samples that did not contain the reagent 9-3 DD and curves identified by circle 82 being the replicate samples with 400 nM of 9-3 DD. The kinetics of fluorescent signals arising from the two sets of samples demonstrates that total double-stranded DNA accumulated somewhat more rapidly in the absence of reagent 9-3 DD than in the presence of the reagent, but the total amount of double-stranded DNA accumulated by 60 cycles is virtually identical in the two sets of reactions.

Panel B of FIG. 8 shows the electrophoretic gels with ethidium bromide staining. On the left, lane a is the size marker (50 base-pair differences), and lanes b through i are samples without reagent 9-3 DD. On the right, lanes j thru q are samples with 400 nM 9-3 DD, and lane r is the size marker. The results show that reactions that did not contain the reagent according to this invention generated the correct product as well as many non-specific products of higher molecular weight, while the reactions that contained reagent 9-3 DD generated only the correct product. Moreover, reactions that contained reagent 9-3 DD generated about twice as much of the correct product as reactions that did not, as judged by the relative intensities of the correct product band in the gels.

In combination the kinetic analysis and the electrophoretic analysis reveal that reactions 81 that generate non-specific products produce fluorescent signals sooner than reactions 82 that generate only the correct product. SYBR Green dye intercalates into double stranded DNA without regard to sequence specificity. Thus the sigmoidal kinetics of the reactions 82, as compared to the more rectilinear kinetics in reactions 81 can be used to judge whether a symmetric reaction is or is not accumulating only the correct product.

Example 9

Quantification of Exonuclease Inhibition

This example describes a rigorous assay for measuring the inhibitory effect of a reagent according to this invention on the 5'-3' exonuclease activity of Taq DNA polymerase. This assay uses a similar primer-template system described by M. W. Kaiser, N. Lyamicheva, W. Ma, C. Miller, B. Neri, L. Fors, and V. I. Lyamicheva in J. Bio. Chem., 274, pp. 21387-21394 (1999), except that the template is labeled with Cy5 at the 5' end and the assay is carried out in the presence of SYBR Green I, a DNA dye that fluoresces when bound to double-stranded DNA. The template for this assay consists of the oligonucleotide sequence 5'-Cy5-AAAACGCTGTCTCGCTGAAAGCGAGA-CAGCGAAAGACGCTCGT-3' (SEQ ID NO: 35) annealed to a primer with the nucleotide sequence:

5'-ACGAGCGTCTTTC-3' (SEQ ID NO: 36). The longer oligonucleotide forms a hairpin structure with two single-stranded tails of different lengths. The shorter 5' tail of the template contains the Cy5 fluorophore and consists of 4 adenosine residues; the longer 3' tail of the template serves as the target for the primer oligonucleotide such that the primer sits directly in front of the 5' template tail with one base pair overlap. Addition of SYBR Green I to this template-primer complex results in SYBR Green I binding to the double-stranded DNA regions of the complex. Upon SYBR Green I excitation with a 480 nm laser, fluorescence energy from the bound DNA dye is completely absorbed by Cy5, which is believed to occur via fluorescence resonance energy transfer, and there is no detectable fluorescence at the maximum SYBR Green emission wavelength (maximum emission wavelength: 521 nm). Hydrolysis of the 5' tail by the 5'-3' exonuclease activity of Taq polymerase results in removal of the Cy5 moiety from the template-primer complex and restoration of detectable SYBR Green I fluorescence. The kinetics of SYBR Green I fluorescence restoration in the presence of Taq DNA polymerase provides a quantitative measure of 5'-3' exonuclease activity. Reagents according to this invention inhibit the 5'-3' exonuclease activity of Taq polymerase and slow down SYBR Green I fluorescence increase.

The assay consisted of 0.5 µM of the above template and 1.5 µM of the above primer mixed in 1×PCR buffer, 3 mM $MgCl_2$, a 1:40000 dilution of a commercial SYBR Green I stock (Molecular Probes, Eugene, Oreg.), 1.25 U Taq polymerase (Invitrogen, Calrsbad, Calif.) in the absence or the presence of 9-22 DD compound at 50 nM, 100 nM, 300 nM, or 1000 nM in a volume of 25 microliters (µl). There was no addition of dNTPs in the reaction mix, because the assay does not rely on DNA polymerase activity. The reaction mixture minus the template and primer was set up at 25° C. to promote the interaction between the 9-22 DD compound and Taq DNA polymerase. The sample was then placed on ice, supplemented with template and primers, and kept on ice until the start of the reaction. Negative controls lacked Taq DNA polymerase. The reaction was initiated by incubating the sample at 25° C. in an ABI Prism Sequence Detector 7700 for 60 minutes with fluorescence collection in the SYBR Green I channel every 30 seconds. Three different trials were averaged for each control and for each concentration of reagent 9-22 DD.

FIG. 9 presents the results of the assay. Detectable SYBR Green I fluorescence provides a measure of the extent of 5'-3' exonuclease activity. The "No Taq" control shows no SYBR fluorescence signal consistent with complete absorption of SYBR Green I fluorescence by Cy 5 and complete absence of 5'-3' exonuclease activity (line 96). Addition of Taq polymerase restores SYBR Green I fluorescence and provides a baseline for the maximum levels of 5'-3' exonuclease activity under the assay conditions (line 91). Addition of 9-22 DD compound to the reaction mix slows down restoration of SYBR-Green I fluorescence in a dosage-dependent manner due the inhibitory effect of 9-22 DD on the 5'-3' exonuclease activity of Taq polymerase (line 92, 50 nM; line 93, 100 nM; line 94, 300 nM; line 95, 1000 nM). Table III below quantifies the percentage inhibition of 5'-3' exonuclease activity by various concentrations of the 9-22 DD compound based on the relative SYBR Green I fluorescence levels achieved after 60 minute incubation at 25° C.

TABLE III

| Reaction | Fluorescence | % 5'-3' Exonuclease Inhibition |
| --- | --- | --- |
| No 9-22DD | 1378 units | 0.0 |
| 50 nM 9-22DD | 1315 units | 4.6 |
| 100 nM 9-22DD | 1155 units | 16.2 |
| 300 nM 9-22DD | 989 units | 28.2 |
| 1000 nM 9-22DD | 624 units | 54.7 |
| No Taq: | 0 units | No 5'-3' exonuclease activity |

Example 10

Preventing Primer-Dimer Formation and Oligomerization in the Presence and Absence of Target DNA A series of LATE-PCR amplification reactions were set up in the presence or absence of 100 genomes human placental DNA (Sigma, St Louis, Mo.) in a final volume of 25 ul. In this experiment, LATE-PCR amplification reactions consisted of 1×PCR buffer (Invitrogen, Carlsbad, Calif.), 3 mM MgCl$_2$, 0.25 mM dNTP, 1000 nM Excess Primer, 50 nM Limiting Primer, 0.25 uM FAM-labeled probe strand, 0.3 uM Dabcyl-labeled reverse complement strand, 1.25 units Platinum Taq DNA polymerase (Invitrogen, Carlsbad, Calif.). The sequence of the primers and probes were as follows:

```
Excess Primer:
5' GTTTCTTTGCTGCCGTGTTC 3'          (SEQ ID NO:37)

Limiting Primer:
5' CCCCAGAGACCCCAGTTGCTAACCAGAC 3'  (SEQ ID NO:38)

FAM-labeled probe strand:
5' [TET] AGACAGAGTTGAAAGTCAGG [Phos] (SEQ ID NO:39)
3'

Dabcyl-labeled reverse complement
strand:
5' ACTTTCAACTCTGTCT [Dabcyl] 3'     (SEQ ID NO:40)
```

These primers and probes amplify and detect a 488 base-pair (bp) amplicon that encompasses exons 5 and 6 of the human p53 gene.

Amplification was carried out in an ABI Prism 7700 Sequence Detector (Applied Biosystems, Calif.) with a thermal profiles that consisted of 1 cycle at 95° C. for 3 minutes; 25 cycles at 95° C. for 10 sec, 64° C. for 30 sec, 75° C. for 30 sec; and 35 cycles at 95° C. for 10 sec, 64° C. for 30 sec, 75° C. for 30 sec, 45° C. for 20 sec with fluorescence detection in the TET channel during the 45° C. step.

Figure 10:
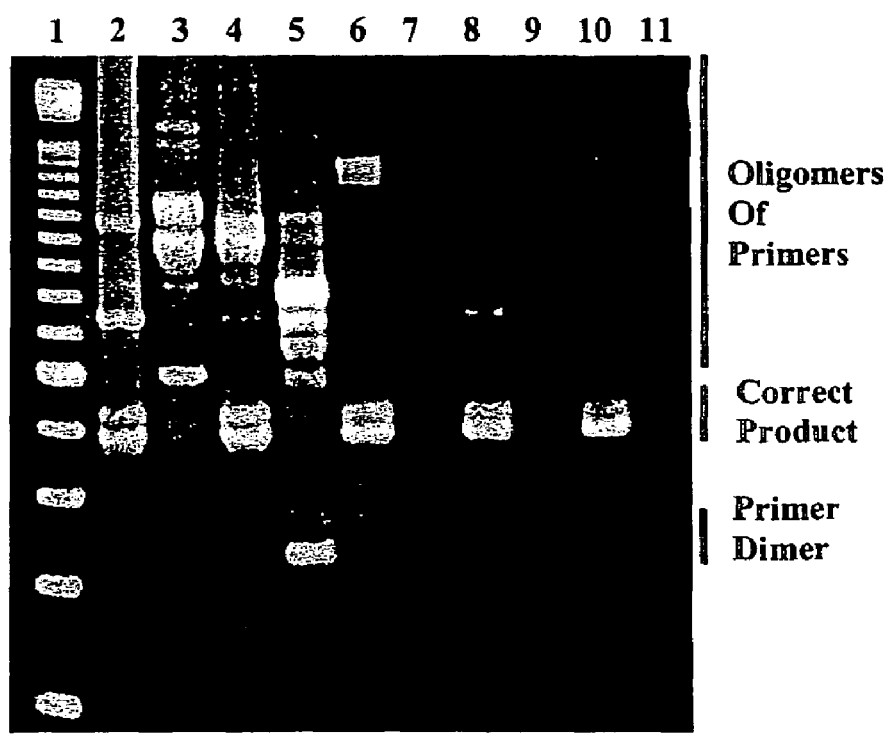
FIG. 10 shows the dose-dependent effect of a reagent according to this invention on formation of primer-dimers and primer oligomers in a LATE-PCR amplification.

The resulting amplification products were analyzed by gel electrophoresis in a 3% agarose gel in 0.5×TBE buffer for 2 hours and stained with ethidium bromide. Results are shown in FIG. 10. The samples in lanes 3, 5, 7, 9, 11 had been prepared without genomic DNA. The samples in lanes 2, 4, 6, 8, 10 had been prepared with genomic DNA. Lane 1 contained electrophoretic size markers in a 100 base-pair ladder. Reagent 9-22 DD was added to the starting reactions as follows: lanes 2 and 3, 0 nM; lanes 4 and 5, 50 nM; lanes 6 and 7, 100 nM; lanes 8 and 9, 200 nM; lanes 10 and 11, 300 nM.

Adjacent to the right side of the gel we have marked the size of correct product and also sizes that we infer to be primer-dimers and oligomers of primer. The results presented in FIG. 10 demonstrate that in reactions initiated with genomic DNA increasing the concentration of reagent 9-22 DD acts in a dosage-dependent manner to prevent manifestation of non-specific products, including primer-dimers and primer oligomers and thereby increases both the specificity and yield of the correct products. Increasing concentrations of reagent 9-22 DD also prevent manifestation of primer-dimers and primer oligomers in reactions that do not contain genomic DNA.

Example 11

Preventing Primer-Dimer Formation and in a Duplex Reaction

A series of LATE-PCR amplification reactions was set up in the presence or absence of 100 genomes human placental DNA (Sigma, St Louis, Mo.) in a final volume of 25 μl. In this experiment, LATE-PCR amplification reactions consisted of 1×PCR buffer (Invitrogen, Carlsbad, Calif.), 3 mM MgCl$_2$, 0.20 mM dNTP. Taq polymerase was used at 1.25 units in every sample. A first amplification target sequence (Product 1) was a portion of exon 11 of the Cystic Fibrosis Gene and was amplified with a Limiting Primer: 5' GACGTTTACAGCGAATGCTTGCTAGACCAAT 3' (SEQ ID NO: 41) at 100 nM and an Excess Primer: 5' TCCAAGTTTGCAGAGAAAGACAAT 3' (SEQ ID NO: 42) at 2,000 nM. A second amplification target sequence (Product 2) was a portion of exon 10 of the Cystic Fibrosis Gene and was amplified with a Limiting Primer: 5' CAGTTTTCCTGGATTATGCCTGGCACCAT 3' (SEQ ID NO: 43) at 50 nM and an Excess Primer: 5' GCTTTGATGACGCTTCTGTATCTA 3' (SEQ ID NO: 44) at 1000 nM.

Amplification was carried out in an ABI Prism 7700 Sequence Detector (Applied Biosystems, Calif.) 2 min at 95° C., followed by 25 cycles of 95° C. for 10 sec, 56° C. for 15 sec, 70° C. for 20 sec, followed by 50 cycles of 95° C. for 10 sec, 56° C. for 15 sec, 70° C. for 20 sec, and 45° C. for 30 sec with fluorescence acquisition.

Figure 11:
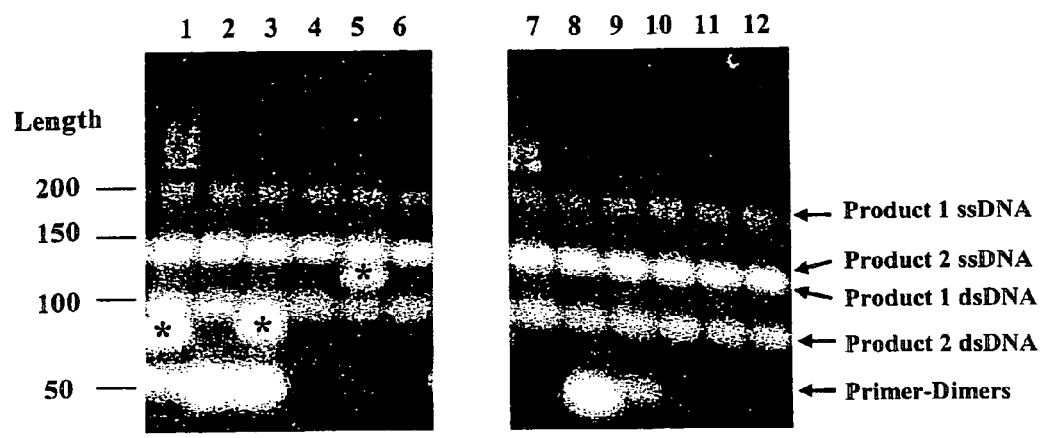
FIG. 11 shows the effect of a low concentration of reagent 9-22 DD on duplex LATE-PCR amplifications of two target sequences with two primer pairs.

The resulting amplification products were analyzed by gel electrophoresis in a 3% agarose gel in 0.5×TBE buffer for 2 hours and stained with ethidium bromide. Results are shown in FIG. 11. Reactions analyzed in lanes 1-6 utilized a non-hot-start Taq polymerase, while reactions analyzed in lanes 7-12 utilized a Taq polymerase plus a hot-start antibody. Reagent 9-22 DD was added to analyzed in lanes reactions 4-6 and 10-12 at 100 nM.

Adjacent to the right side of the gel we have added our interpretation of the identities of the amplification products, including single-stranded amplicons (ssDNA) and double-stranded amplicons (ds DNA) of Product 1 and Product 2, as well as shorter products we infer to be primer-dimers. Other non-specific products are marked with an asterisk. Amplifications with non-hot-start polymerase and no reagent according to this invention, lanes 1-3, produced primer-dimers and other non-specific products. Amplifications with hot-start polymerase and no reagent according to this invention, lanes 7-9, were on the whole somewhat cleaner but still showed a manifestation of mispriming. Addition of reagent according to this invention to the hot-start amplifications, lanes 10-12, produced only the intended products. Addition of reagent according to this invention to the non-hot-start amplifications, lanes 4-6, eliminated primer-dimers and in two of the three repeats (lane 4 and lane 6), all other non-specific products as well, with only one repeat (lane 5) manifesting a non-specific product. The results presented in FIG. 11 demonstrate that a low concentration (100 nM) of reagent 9-22 DD was sufficient to prevent formation of primer-dimers when either non-hot-start Taq polymerase or not-start Taq polymerase was used, and further that that low concentration of reagent 9-22 DD was nearly sufficient to prevent all manifestations of mispriming even when used with non-hot-start Taq polymerase in amplifications of two targets with two primer pairs.

Example 12

Optimizing the Kinetics of a Duplex Real-time PCR and a Real-time PCR by Preventing Primer-Dimer Formation We designed a duplex real-time LATE-PCR assay for simultaneous amplification of sequences within exons of the murine Oct4 and Xist genes (GenBank Accession Number NM_013633 and L04961, respectively). Each reaction was run in a final volume of 50 µl and contained the following reagents: 1×PCR buffer (Invitrogen, Carlsbad, Calif.) comprised by 20 mM Tris-HCl, pH 8.4, and 50 mM KCl, 3 mM MgCl$_2$, 0.4 mM of each dNTP, 50 nM Oct4 Limiting Primer having the sequence 5' TGGCTGGACACCTGGCTTCA-GACT 3' (SEQ ID NO: 45), 2 µM Oct4 Excess Primer having the sequence 5'CAACTTGGGGGACTAGGC 3' (SEQ ID NO: 46), 100 nM Xist Limiting Primer having the sequence 5' GGTCGTACAGGAAAAGATGGCGGCTCAA 3' (SEQ ID NO: 47), 2 µM Xist Excess Primer having the sequence 5' TGAAAGAAACCACTAGAGGGCA 3' (SEQ ID NO: 48), 1 µM Low-T$_m$ Oct4 molecular beacon having the sequence 5' TET-CCG CCT GGG ATG GCA TAC TGT GGA AGG CGG-Dabcyl 3' (SEQ ID NO: 49) and 2 units of antibody-complexed Platinum® Taq DNA polymerase (Invitrogen, Carlsbad, Calif.). Either compound 9-3DD or compound 9-3bDD was also included in the PCR mixture, at the concentrations specified below. A molecular beacon for the detection of Xist amplicons was not added in this example. Each assay also contained the reagents necessary for cell lysis and reverse transcription according to the PurAmp protocol (see Hartshorn et al. (2005) BMC Biotechnol 5: 2, in a 2.5 µl volume. In this duplex LATE-PCR, the final concentrations of such reagents were the following: 2.5 mM Tris acetate, pH 8.4, 3.75 mM potassium acetate and 0.4 mM magnesium acetate (diluted cDNA Synthesis Buffer, ThermoScript™ RT-PCR System, Invitrogen, Carlsbad, Calif.), additional 50 µM of each dNTP, 0.13 mM guanidine isothiocyanate, 6.7 µM β-mercapto-ethanol, 0.7 µM sodium citrate, pH 7.0, 0.7×10$^-$4% (vol/vol) dimethylsulfoxide and 0.2×10$^{-4}$% sarcosyl.

Mouse genomic DNA (Sigma, St Louis, Mo.) was also added to each assay and provided the templates for PCR amplification. The number of genomes added to each tube was calculated based on a 6 pg/genome size (see Vendrely and Vendrely (1949) Experientia 5: 327-329).

Amplification was carried out in an ABI Prism 7700 Sequence Detector (Applied Biosystems, Calif.) with a thermal profile comprised by 1 cycle at 95° C. for 5 minutes; 15 cycles at 95° C. for 10 sec, 63° C. for 20 sec, and 72° C. for 30 sec; and 40 cycles at 95° C. for 15 sec, 55° C. for 25 sec, 72° C. for 35 sec, and 45° C. for 30 sec, with fluorescence acquisition at 45° C. in the TET channel.

At the end of the PCR, amplification products were analyzed by gel electrophoresis in a 3% agarose gel in 0.5×TBE buffer for 2 hours and stained with ethidium bromide. Both the double-stranded and the single-stranded products, of the expected sizes, were visible for the two co-amplified genes, indicating efficient duplex LATE-PCR.

Figure 12:
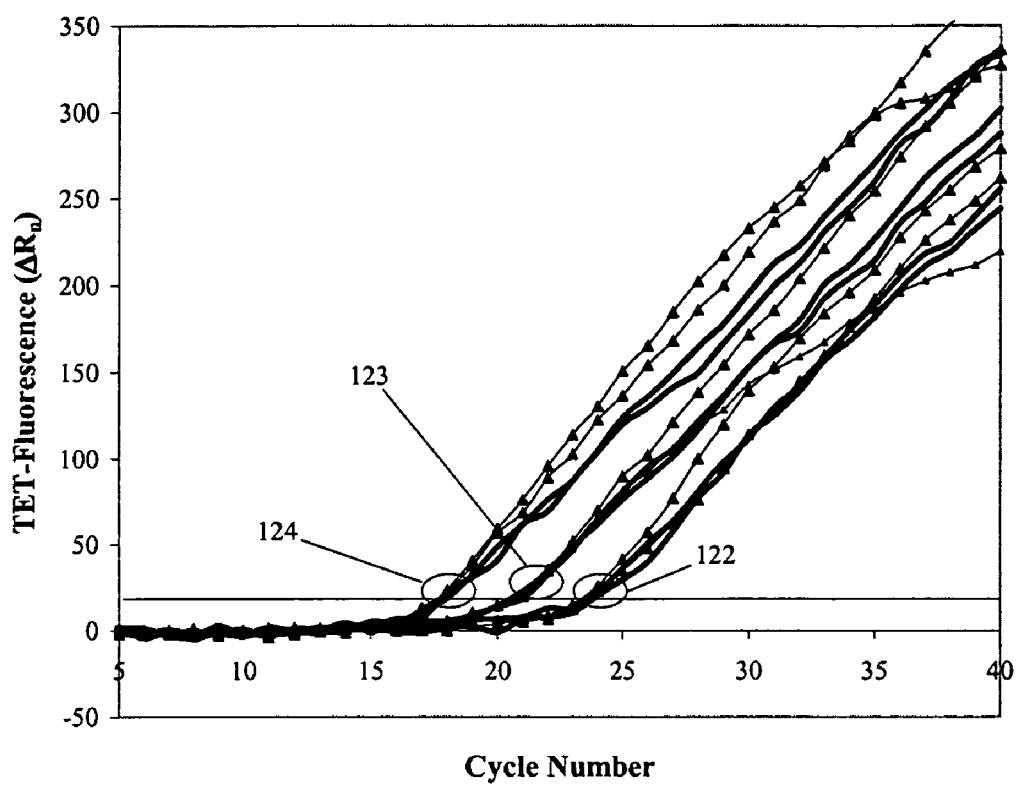
FIG. 12 shows the effect of varying the stem composition of reagent 9-3 DD on a duplex LATE-PCR amplification of two target sequences with two primer pairs.

FIG. 12 illustrates the effect of varying the stem composition of reagent 9-3DD on the kinetics of the duplex LATE-PCR described above, containing two sets of primers for the amplification of two non-homologous sequences within the Oct4 and Xist genes. The figure shows the fluorescent signals generated by accumulating Oct4 amplicons through hybridization with the TET-Oct4 molecular beacon. The results demonstrate that the C$_T$ values are very similar in the presence of 300 nM 9-3DD (lines with triangles) or the same concentration of its modified form 9-3bDD (heavy lines without triangles) at each genome concentration analyzed (10 genomes, circle 122; 100 genomes, circles 123; 1000 genomes, circle 124. The kinetics of the real-time fluorescent signals is, instead, affected by the composition of the reagent's stem. Compound 9-3bDD has a higher-T$_m$ stem compared to 9-3DD, thus, we believe, optimally preventing primer-dimer formation, which in turns results in very linear and parallel signals at all genome concentration tested. In the presence of the less stringent compound 9-3DD, instead, some of the fluorescent signals have a steeper slope but others start plateauing early in the reaction, indicating random formation of primer dimers. Signals generated at different template concentrations with compound 9-3DD are less parallel than those obtained in the presence of compound 9-3bDD (with the modified stem). Linear amplification generating perfectly parallel signals (having a constant slope) is ideally desirable and particularly relevant for end-point types of analysis.

Agarose gel analysis of the samples containing 9-3DD revealed bands, particularly visible at higher template numbers, that may be primer dimers and very small bands at lower template numbers are consistent with primers. Such bands did not appear on the analysis of the samples containing 9-3bDD.

FIG. 13 illustrates the effect of varying the concentration of reagent 9-3bDD in the duplex LATE-PCR described in this example and also used for FIG. 12. In this case, lowering the concentration of reagent 9-3bDD from 300 nM (heavy lines without triangles) to 200 nM (lines with triangles) again affects the slope of linear amplification due to primer-dimer formation, as confirmed by agarose gel analysis. As a result, some of the samples containing low initial template numbers (10 genomes, circle 132) have higher fluorescence at the last cycle ("end point") than samples containing higher initial template numbers (100 genomes, circle 133 and 1000 genomes, circle 134).

The concentration effect of the reagents described in this patent application on PCR efficiency was also tested in a LATE-PCR amplifying one template with one pair of primers. The amplified template was the same murine Oct4 sequence used in the duplex described for FIG. 12 and FIG. 13 and the primers and the molecular beacon sequences were also the same as in that reaction.

Each reaction was run in a final volume of 100 µl and contained the following reagents: 1×PCR buffer (Invitrogen, Carlsbad, Calif.) comprised by 20 mM Tris-HCl, pH 8.4, and 50 mM KCl, 3 mM MgCl$_2$, 0.25 mM of each dNTP, 50 nM Oct4 Limiting Primer, 2 µM Oct4 Excess Primer, 1 µM Low-T$_m$ TET-Oct4 molecular beacon, and 2 units of antibody-complexed Platinum® Taq DNA polymerase (Invitrogen, Carlsbad, Calif.). Compound 9-3DD was also included in the PCR mixture, at concentrations of 150, or 300 or 450 nM. As in the case of the aforementioned duplex (see FIG. 12 and FIG. 13), each assay also contained the reagents necessary for cell lysis and reverse transcription according to the PurAmp protocol, in a 10.5 µl volume. In this LATE-PCR, the final concentrations of such reagents were the following: 5 mM Tris acetate, pH 8.4, 7.5 mM potassium acetate and 0.8 mM magnesium acetate (diluted cDNA Synthesis Buffer), 1 ng/µl Random Hexamers and additional 100 µM of each dNTP (all components of a ThermoScript™ RT-PCR System, Invitrogen, Carlsbad, Calif.), 0.4 mM guanidine isothiocyanate, 20 µM β-mercapto-ethanol, 2 µM sodium citrate, pH 7.0, 2×10⁻⁴% (vol/vol) dimethylsulfoxide and 0.5×10⁻⁴% sarcosyl.

Mouse genomic DNA was also added to each assay and provided the templates for PCR amplification, as specified for the duplex LATE-PCR described in this example. Amplification was again carried out in an ABI Prism 7700 Sequence Detector with the same thermal profile detailed for the duplex reaction. At the end of the PCR, amplification products were analyzed by gel electrophoresis in a 3% agarose gel in 0.5× TBE buffer for 2 hours and stained with ethidium bromide. Both the double-stranded and the single-stranded products were visible on the gel and had the expected sizes, indicating efficient amplification by LATE-PCR.

The effects of increasing concentrations of compound 9-3DD on the amplification efficiency of the Oct4 template were also tested. The $C_T$ values were obtained from real-time PCR assays containing 5 genomes (average of two replicates for each 9-3DD concentration tested), 20 genomes (average of two replicates for each 9-3DD concentration tested), 100 genomes, and 1000 genomes performed with each of the 9-3DD concentrations tested: 150 nM, 300 nM, 450 nM. The linear regression for each $C_T$ point series at each concentration is shown in FIG. 14, where triangles are 450 nM concentration, open squares are 300 nM, and filled squares are 150 nM. It is immediately apparent from this plot that 450 nM 9-3DD greatly delays the appearance of the fluorescent signals above the threshold, also altering the dose-dependence of the PCR amplification (see the points at 10 gene copies and 40 gene copies, distant from the line of regression). The $C_T$ values obtained using 150 nM or 300 nM 9-3DD, on the other hand, are very similar and demonstrate a linear relationship between template copy number and fluorescent signal first appearance.

Analysis of the real-time patterns of fluorescence, however, highlights a difference between the two conditions (concentrations) as illustrated in FIG. 15. The slope of the curves generated by either 100 genomes, circle 151, or 1000 genomes, circle 152, is steeper when using 300 nM 9-3DD (heavy lines with no triangles) than when using 150 nM 9-3DD (lines with triangles), suggesting that the more stringent conditions, 300 nM, eliminate primer dimers, thus increasing amplification efficiency.

Example 13

Use of Multiple Reagents According to this Invention

LATE-PCR reaction mixtures were prepared to amplify five different target sequences of human genomic DNA starting material individually and to amplify all five together in a multiplex reaction. Each target sequence required its own pair of limiting and excess primers. The target sequences were (1) a 191-base pair Globin allele, (2) a 312 base-pair Tay Sachs G269 allele, (3) a 452 base-pair Tay Sachs 1278 and 1421 allele, (4) a 549 base-pair segment of Mitochondrial hypervariable region 1, and (5) a 611 base-pair segment comprising p53 gene exons 7 and 8. The 25 µl reaction mixtures contained 1×PCR buffer (Invitrogen), 0.4 mM dNTPs, 3 mM Mg++, 0.24×SYBR Green and 1.5 units of Taq DNA polymerase (Invitrogen). Primers were added at a concentration of 50 nM for Limiting Primer and 1000 nM for Excess Primer. All five primer pairs were added to the multiplex reactions. Thermal cycling was forty-five cycles of 95° C. for 10 sec, 64° C. for 20 sec, and 72° C. for 1 min.

Both the reaction mixtures with individual primer pairs and individual targets, and the reaction mixtures with all five primer pairs and all five targets were amplified in the presence of a combination of 25 nM compound 9-22DD and 100 nM compound 12-3DD. The pentaplex reaction mixture was amplified also without addition of any reagent according to this invention. Reaction products were examined by gel electrophoresis. Gel electrophoresis results of the various amplifications are shown in FIG. 16, which includes size markers (100 base-pair differences) in lane r. Central lanes g-k are the products of individual amplifications of target sequences (1)-(5), respectively. Lanes 1-q are the products of six replicate pentaplex amplifications that included the mixture of compound 9-22DD and compound 12-3DD. Lanes a-f are the products of six replicate pentaplex amplifications that included no reagent according to this invention. FIG. 16 shows that the mixture of compounds enhanced amplification (more and cleaner desired amplicons) as compared to the multiplex reaction without addition of any compound, demonstrating that mixtures of reagents may be used in kits, amplifications and assays of this invention.

Example 14

Testing Modes of Action

We have devised a test to investigate quantitatively the mispriming reduction (specificity improvement) and polymerase-inhibiting effects of reagents according to this invention, which we believe distinguishes First Mode from Third Mode action. The test is a PCR amplification assay essentially similar to the assay described in Example 1, with the following exceptions: the amplification reaction mixture contains half (1000 genomes) of the sheared genomic DNA, and the final portion of thermal cycling is reduced from 70 cycles to 40 cycles. Amplifications are performed with the addition of varying amounts of reagent according to this invention, typically 25 nM, 50 nM, 100 nM, 300 nM, 1500 nM and 3000 nM. The test includes two analyses: first, for specificity, a melting curve of the amplified product; and, second, for inhibition, a real-time fluorescence curve of double-stranded product being synthesized.

Figure 17:
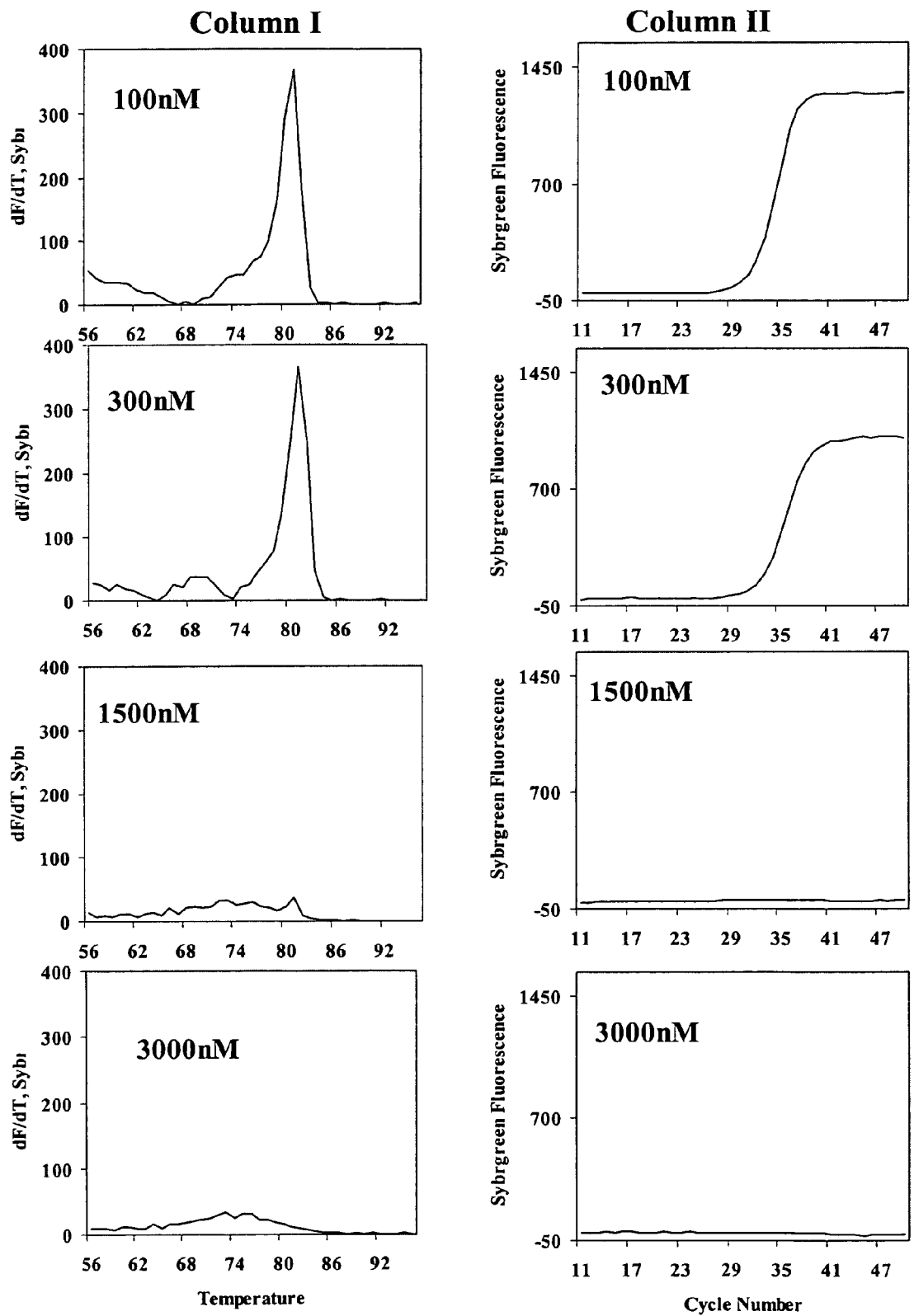
FIG. 17 shows the results of a test for the action of compound 12-3DD.
Figure 18:
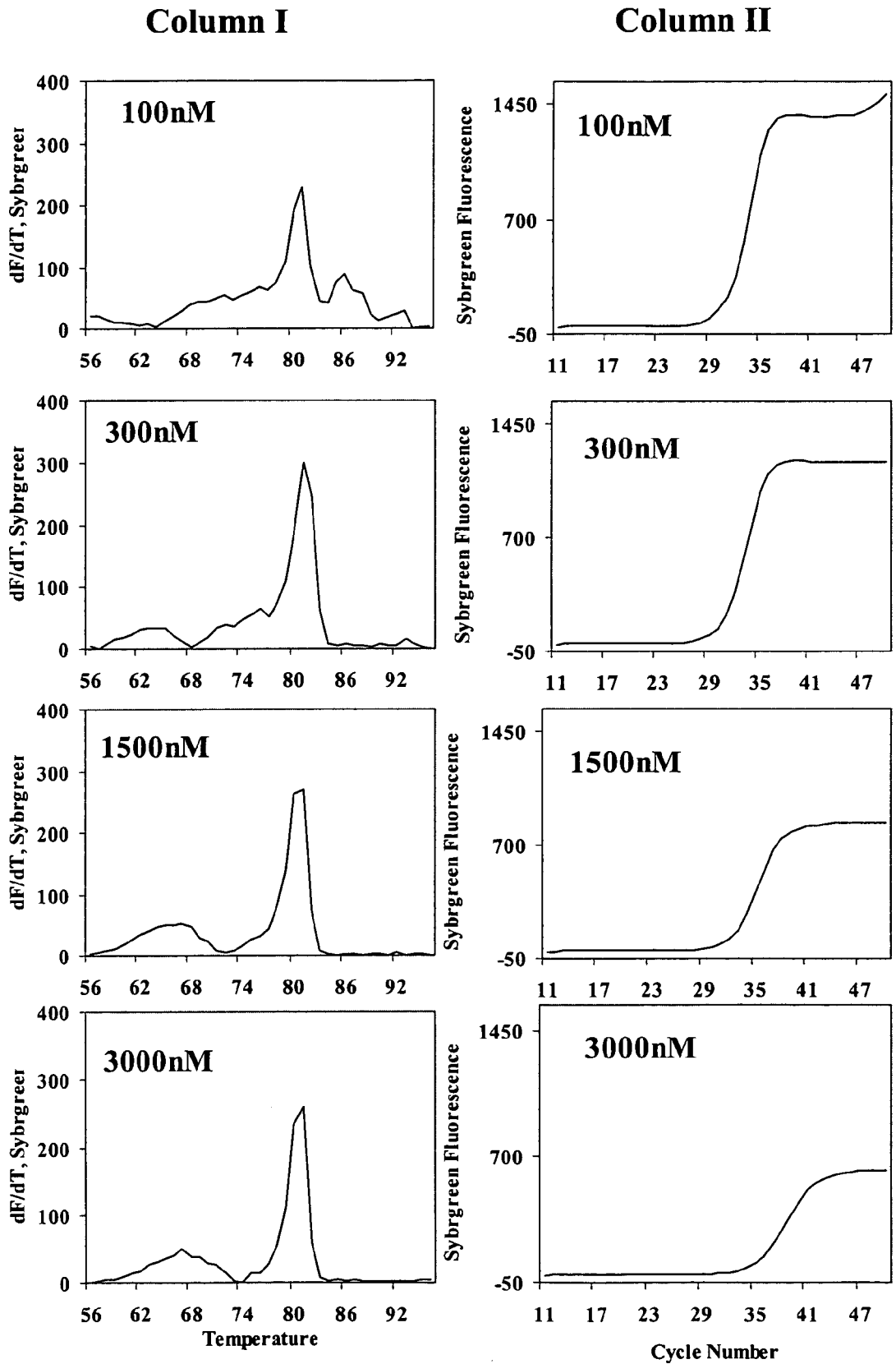
FIG. 18 shows the results of a test for the action of compound 12-C3DD.

FIGS. 17-18 present portions of the analytical results for two reagents according to this invention, compound 12-3DD and compound 12-C3DD, respectively. In each figure Column I presents melting curves for several selected concentrations of reagent, as indicated. In each figure Column II presents real-time florescence curves for the same concentrations, as indicated. Referring to FIG. 17, Column I, melting curves showed that compound 12-3DD achieved high specificity (avoiding mispriming) at concentrations of 100 nM and above (the lowest concentration, 100 nM, being slightly higher than found for the reaction described in Example 1). Referring to FIG. 17, Column II, real-time fluorescence curves showed that polymerase inhibition increased progressively as the concentration of compound 12-3DD was increased above 100 nM until the reaction was essentially shut down at concentrations above 1000 nM. Inhibition is reflected in the lower amount of total double-stranded product(s) generated (including the desired specific product and non-specific products of mispriming) indicated by the plateau florescence level, and by the delay in the $C_T$ value (19.6 for 100 NM, 21.1 for 300 nM, and nonexistent, that is, at least 40 for 1500 nM and 3000 nM). Referring to FIG. 18, Column I, melting curves showed that compound 12-3DD achieved high specificity at concentrations of 300 nM and above (the lowest concentration, 300 nM, being the same as found for the reaction described in Example 1). Referring to FIG. 18, Column II, real-time fluorescence curves showed that polymerase inhibition increased progressively as the concentration of compound 12-C3DD was increased above 300 nM ($C_T$ values were 18.8 for 100 nM, 18.8 for 300 nM, 21.1 for 1500 nM and 24.5 for 300 nM) but that the reaction was not shut down even at a concentration of 3000 nM.

Comparing FIG. 18 and FIG. 18, it can be seen that the overall performance of comp9ound 12-C3DD is less concentration dependent than the overall performance of compound 12-3DD. Thus, for this particular amplification reaction, the $C_T$ delay and plateau florescence decrease resulting as compound 12-C3DD concentration goes from 300 nM to 1500 nM are roughly the same as result as compound 12-3DD concentration goes from 100 nM to 300 nM.

A number of embodiments of the invention have been described. Nevertheless, it will be understood that various modifications may be made without departing from the spirit and scope of the invention. Accordingly, other embodiments are within the scope of the following claims.

What is claimed is:

1. A reagent capable of preventing at least one manifestation of mispriming in a polymerase chain reaction (PCR) amplification to produce at least one amplified DNA product when added at a concentration of not more than 650 nM to a PCR amplification mixture that includes 1.25 units of a thermostable DNA polymerase per 25 pA of reaction mixture, said reagent being an oligonucleotide that has a 3' end and a stem-loop structure having a stem comprising a double-stranded region that has a length is greater than six nucleotides and a terminus away from the loop comprising a 3' nucleotide and a 5' nucleotide, said stem having a calculated stem melting temperature (Tm) below 94° C.,
wherein
  a) the 3' end is non-extendable by said DNA polymerase,
  b) the oligonucleotide is not fluorescently labeled and does not contribute background fluorescence, and
  c) said stem terminus is stabilized by means selected from the group consisting of non-fluorescent fluorophore-iuenching moieties covalently attached to the 3' and 5' nucleotides of said stem terminus and pairs of non-natural nucleotides that bind more strongly than a natural DNA-DNA hybrid and that include each of the 3' and 5' nucleotides of said stem terminus.

2. The reagent according to claim 1, wherein the stem-stabilization means are non-fluorescent fluorophore-quenching moieties.

3. The reagent according to claim 1, wherein the loop is selected from the group consisting of an oligonucleotide comprising at least three nucleotides and a non-nucleotide chemical linker.

4. The reagent according to claim 3, wherein the chemical linker is a methylene bridge of 3-6 carbon atoms.

5. The reagent according to claim 1, wherein the stem comprises a double-stranded region of 9-12 base pairs.

6. The reagent according to claim 5, wherein the stem is blunt ended and contains no internal mismatches.

7. The reagent according to claim 1, wherein the stem has a calculated melting temperature (Tm) in a range selected from the group consisting of 72-85° C. and 50-71° C.

8. The reagent according to claim 7, wherein the stem-stabilization means are non-fluorescent fluorophore-quenching moieties.

9. The reagent according to claim 1, wherein the stem-stabilization means are pairs of 2'-O-methyl nucleotides.

10. The reagent according to claim 9, wherein the loop is selected from the group consisting of an oligonucleotide comprising at least three nucleotides and a non-nucleotide chemical linker.

11. The reagent according to claim 9, wherein the stem comprises a double-stranded region of 9-12 base pairs.

12. A set of oligonucleotides for performing a polymerase chain reaction (PCR) amplification comprising at least one pair of PCR primers and at least one reagent according to claim 1.

13. The set according to claim 12, further comprising at least one fluorescently labeled probe that hybridizes to the amplified product defined by said at least one pair of PCR primers.

14. The set according to claim 12, wherein the stem-stabilizing means are non-fluorescent fluorophore-quenching moieties.

15. A kit of reagents for performing a polymerase chain reaction (PCR) amplification comprising a thermostable DNA polymerase, at least one pair of PCR primers, dNTPs and at least one mispriming prevention reagent according to claim 1.

16. The kit according to claim 15, further comprising reagents for nucleic acid isolation.

17. The kit according to claim 15, wherein the mispriming prevention reagent has a stem comprising a double-stranded sequence of 9-12 nucleotides.

18. The kit according to claim 15, wherein the stem-stabilization means are non-fluorescent fluorophore-quenching moieties.

19. The kit according to claim 15, wherein the mispriming prevention reagent has a stem with a calculated melting temperature (Tm) in a range selected form the group consisting of 72-85° C. and 50-71° C.

* * * * *

UNITED STATES PATENT AND TRADEMARK OFFICE
CERTIFICATE OF CORRECTION

PATENT NO. : 7,517,977 B2  Page 1 of 1
APPLICATION NO. : 11/252506
DATED : April 14, 2009
INVENTOR(S) : Lawrence J. Wangh et al.

It is certified that error appears in the above-identified patent and that said Letters Patent is hereby corrected as shown below:

ON THE TITLE PAGE

Item (60) the Related U.S. Application Data has been omitted, it should read:

-- Related U.S. Application Data

(60) Provisional application No. 60/619,670, filed on October 18, 2004. --

Signed and Sealed this

Sixteenth Day of June, 2009

JOHN DOLL
*Acting Director of the United States Patent and Trademark Office*

```
SEQUENCE LISTING

<160> NUMBER OF SEQ ID NOS: 50

<210> SEQ ID NO 1
<211> LENGTH: 34
<212> TYPE: DNA
<213> ORGANISM: Artificial Sequence
<220> FEATURE:
<223> OTHER INFORMATION: synthetically generated oligonucleotide

<400> SEQUENCE: 1
ggcgtcaggc atataggata ccgggacaga cgcc                              34

<210> SEQ ID NO 2
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 2
cattataatg aaattataat g                                            21

<210> SEQ ID NO 3
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 3
cgcggcgtca tatagacgcc gcg                                          23

<210> SEQ ID NO 4
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 4
cgcggcgtca ggcatatagg ataccgggac agacgccgcg                        40

<210> SEQ ID NO 5
<211> LENGTH: 44
<212> TYPE: DNA
<213> ORGANISM: Artificial Sequence
<220> FEATURE:
<223> OTHER INFORMATION: synthetically generated oligonucleotide

<400> SEQUENCE: 5
gctcgctgcc gaccgtatat cctatggccc tgacggcagc gagc                   44

<210> SEQ ID NO 6
<211> LENGTH: 27
<212> TYPE: DNA
```

```
<213> ORGANISM: Artificial Sequence
<220> FEATURE:
<223> OTHER INFORMATION: synthetically generated oligonucleotide

<400> SEQUENCE: 6
cttaattata atgaaattat aattaag                                          27

<210> SEQ ID NO 7
<211> LENGTH: 24
<212> TYPE: DNA
<213> ORGANISM: Artificial Sequence
<220> FEATURE:
<223> OTHER INFORMATION: synthetically generated oligonucleotide
<220> FEATURE:
<221> NAME/KEY: misc_structure
<222> LOCATION: (12)...(13)
<223> OTHER INFORMATION: (CH2)3 between position 12 and 13

<400> SEQUENCE: 7
cttaattata atattataat taag                                             24

<210> SEQ ID NO 8
<211> LENGTH: 24
<212> TYPE: DNA
<213> ORGANISM: Artificial Sequence
<220> FEATURE:
<223> OTHER INFORMATION: synthetically generated oligonucleotide
<220> FEATURE:
<221> NAME/KEY: misc_structure
<222> LOCATION: (12)...(13)
<223> OTHER INFORMATION: (CH2)3(CH2)3 between position 12 and 13

<400> SEQUENCE: 8
cttaattata atattataat taag                                             24

<210> SEQ ID NO 9
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 9
cgttataatg aaattataac g                                                21

<210> SEQ ID NO 10
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 10
cgctataatg aaattatagc g                                                21

<210> SEQ ID NO 11
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 11
cgtaattata atgaaattat aattacg                                          27

<210> SEQ ID NO 12
<211> LENGTH: 27
```

```
<212> TYPE: DNA
<213> ORGANISM: Artificial Sequence
<220> FEATURE:
<223> OTHER INFORMATION: synthetically generated oligonucleotide

<400> SEQUENCE: 12
cgctattata atgaaattat aatagcg                                      27

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
ctttgatgac gcttctgtat cta                                          23

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
cctggattat gcctggcacc at                                           22

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
cgaggtcatt gaatacgcac ggctcc                                       26

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
taacaagcag agtccctctg gt                                           22

<210> SEQ ID NO 17
<211> LENGTH: 22
<212> TYPE: DNA
<213> ORGANISM: Artificial Sequence
<220> FEATURE:
<223> OTHER INFORMATION: probe

<400> SEQUENCE: 17
taacaagcag agtccctctg gt                                           22

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
```

-continued

```
gccaggggtt ccactacgta ga                                                22
```

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19

```
ccgcccttct ctctgccccc tggt                                              24
```

<210> SEQ ID NO 20
<211> LENGTH: 26
<212> TYPE: DNA
<213> ORGANISM: Artificial Sequence
<220> FEATURE:
<223> OTHER INFORMATION: probe

<400> SEQUENCE: 20

```
cgtgcgctct ggtaagggtt tgcacg                                            26
```

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21

```
gccaggggtt ccactacgta ga                                                22
```

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22

```
ccgcccttct ctctgccccc tggt                                              24
```

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23

```
ccgggtctct aagggagaac tcct                                              24
```

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24

```
ccggccgaca acacaaacct ggtcc                                             25
```

<210> SEQ ID NO 25
<211> LENGTH: 24
<212> TYPE: DNA
<213> ORGANISM: Artificial Sequence

```
<220> FEATURE:
<223> OTHER INFORMATION: primer

<400> SEQUENCE: 25
gctttgatga cgcttctgta tcta                                          24

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
cagttttcct ggattatgcc tggcaccat                                     29

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
tcgaagtttg cagagaaaga caat                                          24

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
tgacgtttac agcgaatgct tgctagacca at                                 32

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
tgggtttctg atacgcactg actctctc                                      28

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
ggccatcact aaaggcaccg agcact                                        26

<210> SEQ ID NO 31
<211> LENGTH: 18
<212> TYPE: DNA
<213> ORGANISM: Artificial Sequence
<220> FEATURE:
<223> OTHER INFORMATION: DNA template

<400> SEQUENCE: 31
agtgtgatga tggtgagg                                                 18
```

<210> SEQ ID NO 32
<211> LENGTH: 16
<212> TYPE: DNA
<213> ORGANISM: Artificial Sequence
<220> FEATURE:
<223> OTHER INFORMATION: DNA template

<400> SEQUENCE: 32
actttcaact ctgtct                                                    16

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
taattacaag agtcttccat                                                20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
catgaataga acatttcctt                                                20

<210> SEQ ID NO 35
<211> LENGTH: 43
<212> TYPE: DNA
<213> ORGANISM: Artificial Sequence
<220> FEATURE:
<223> OTHER INFORMATION: DNA template

<400> SEQUENCE: 35
aaaacgctgt ctcgctgaaa gcgagacagc gaaagacgct cgt                      43

<210> SEQ ID NO 36
<211> LENGTH: 13
<212> TYPE: DNA
<213> ORGANISM: Artificial Sequence
<220> FEATURE:
<223> OTHER INFORMATION: primer

<400> SEQUENCE: 36
acgagcgtct ttc                                                       13

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gtttctttgc tgccgtgttc                                                20

<210> SEQ ID NO 38
<211> LENGTH: 28
<212> TYPE: DNA
<213> ORGANISM: Artificial Sequence
<220> FEATURE:
<223> OTHER INFORMATION: primer

<400> SEQUENCE: 38
ccccagagac cccagttgct aaccagac         28

<210> SEQ ID NO 39
<211> LENGTH: 20
<212> TYPE: DNA
<213> ORGANISM: Artificial Sequence
<220> FEATURE:
<223> OTHER INFORMATION: probe

<400> SEQUENCE: 39
agacagagtt gaaagtcagg         20

<210> SEQ ID NO 40
<211> LENGTH: 16
<212> TYPE: DNA
<213> ORGANISM: Artificial Sequence
<220> FEATURE:
<223> OTHER INFORMATION: probe

<400> SEQUENCE: 40
actttcaact ctgtct         16

<210> SEQ ID NO 41
<211> LENGTH: 31
<212> TYPE: DNA
<213> ORGANISM: Artificial Sequence
<220> FEATURE:
<223> OTHER INFORMATION: primer

<400> SEQUENCE: 41
gacgtttaca gcgaatgctt gctagaccaa t         31

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
tccaagtttg cagagaaaga caat         24

<210> SEQ ID NO 43
<211> LENGTH: 29
<212> TYPE: DNA
<213> ORGANISM: Artificial Sequence
<220> FEATURE:
<223> OTHER INFORMATION: primer

<400> SEQUENCE: 43
cagttttcct ggattatgcc tggcaccat         29

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
gctttgatga cgcttctgta tcta         24

<210> SEQ ID NO 45

-continued

```
<211> LENGTH: 24
<212> TYPE: DNA
<213> ORGANISM: Artificial Sequence
<220> FEATURE:
<223> OTHER INFORMATION: primer

<400> SEQUENCE: 45
tggctggaca cctggcttca gact                                              24

<210> SEQ ID NO 46
<211> LENGTH: 18
<212> TYPE: DNA
<213> ORGANISM: Artificial Sequence
<220> FEATURE:
<223> OTHER INFORMATION: primer

<400> SEQUENCE: 46
caacttgggg gactaggc                                                     18

<210> SEQ ID NO 47
<211> LENGTH: 28
<212> TYPE: DNA
<213> ORGANISM: Artificial Sequence
<220> FEATURE:
<223> OTHER INFORMATION: primer

<400> SEQUENCE: 47
ggtcgtacag gaaaagatgg cggctcaa                                          28

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
tgaaagaaac cactagaggg ca                                                22

<210> SEQ ID NO 49
<211> LENGTH: 30
<212> TYPE: DNA
<213> ORGANISM: Artificial Sequence
<220> FEATURE:
<223> OTHER INFORMATION: probe

<400> SEQUENCE: 49
ccgcctggga tggcatactg tggaaggcgg                                        30

<210> SEQ ID NO 50
<211> LENGTH: 93
<212> TYPE: DNA
<213> ORGANISM: Artificial Sequence
<220> FEATURE:
<223> OTHER INFORMATION: DNA template

<400> SEQUENCE: 50
attgggaagg tggttgagag ggaccctgga gttaccccac catcaccaga ctgttgttgc       60
ttgttttccc tcaggtaccc ctgagcagaa ggc                                    93
```